(12) United States Patent
Hashimshony et al.

(10) Patent No.: US 8,721,565 B2
(45) Date of Patent: May 13, 2014

(54) DEVICE FOR FORMING AN EFFECTIVE SENSOR-TO-TISSUE CONTACT

(75) Inventors: Dan Hashimshony, Givat Ada (IL); Gil Cohen, Jerusalem (IL); Iddo Geltner, Herzlia (IL)

(73) Assignee: Dune Medical Devices Ltd., Caesaria (IL)

( * ) Notice: Subject to any disclaimer, the term of this patent is extended or adjusted under 35 U.S.C. 154(b) by 856 days.

(21) Appl. No.: 11/196,732

(22) Filed: Aug. 4, 2005

(65) Prior Publication Data

US 2007/0032739 A1 Feb. 8, 2007

(51) Int. Cl.
*A61B 5/00* (2006.01)

(52) U.S. Cl.
USPC .......................................... 600/587; 600/363

(58) Field of Classification Search
USPC ................................. 600/587, 363
See application file for complete search history.

(56) References Cited

U.S. PATENT DOCUMENTS

| | | | |
|---|---|---|---|
| 3,830,224 A | | 8/1974 | Vanzetti et al. |
| RE30,317 E | * | 7/1980 | Lubbers et al. ............... 600/363 |
| 4,291,708 A | | 9/1981 | Frei et al. |
| 4,344,440 A | | 8/1982 | Aaby et al. |
| 4,458,694 A | | 7/1984 | Sollish et al. |
| 4,537,203 A | | 8/1985 | Machida |
| 4,539,640 A | | 9/1985 | Fry et al. |
| RE32,000 E | | 10/1985 | Sagi |
| 4,617,939 A | | 10/1986 | Brown et al. |
| 4,625,171 A | | 11/1986 | Sekihara et al. |
| 4,682,594 A | | 7/1987 | Mok |
| 4,689,567 A | | 8/1987 | Maudsley |
| 4,751,464 A | | 6/1988 | Bridges |
| 4,768,513 A | | 9/1988 | Suzuki |
| 4,779,624 A | | 10/1988 | Yokoi |
| 4,785,806 A | | 11/1988 | Deckelbaum |
| 5,115,137 A | | 5/1992 | Andersson-Engels et al. |
| 5,143,079 A | | 9/1992 | Frei et al. |
| 5,227,730 A | | 7/1993 | King et al. |
| 5,277,730 A | | 1/1994 | Darsey et al. |

(Continued)

FOREIGN PATENT DOCUMENTS

| | | |
|---|---|---|
| DE | 19705260 A1 | 8/1997 |
| DE | 19734978 A1 | 2/1999 |

(Continued)

OTHER PUBLICATIONS

Rajshekhar "Continuous Impedence Monitoring During CT-Guided Stereotactic Surgery: Relative Value in Cystic and Solid Lesions", British Journal of Neurosurgery, 6: 439-444, 1992.

(Continued)

*Primary Examiner* — Rene Towa
*Assistant Examiner* — Emily Lloyd

(57) ABSTRACT

A device for tissue characterization, comprises a structure; a first mechanism, associated with the structure, configured for exerting a first force on a tissue, for fixing the tissue to the structure, so as to substantially immobilize the tissue; and a second mechanism, associated with the structure, configured for pressing a sensor against an external surface of the immobilized tissue, thereby exerting a second force on the immobilized tissue, wherein at least a component of the first force is in opposition to at least a component of the second force, forcing the immobilized tissue against the sensor, and forcing the sensor against the immobilized tissue, bringing about an effective contact between the sensor and the immobilized tissue.

23 Claims, 15 Drawing Sheets

(56) References Cited

U.S. PATENT DOCUMENTS

| | | |
|---|---|---|
| 5,334,941 A | 8/1994 | King |
| 5,383,454 A | 1/1995 | Bucholz |
| 5,442,290 A | 8/1995 | Crooks |
| 5,482,041 A | 1/1996 | Wilk et al. |
| 5,482,047 A | 1/1996 | Nordgren et al. |
| 5,558,092 A | 9/1996 | Unger et al. |
| 5,572,132 A | 11/1996 | Pulyer et al. |
| 5,574,815 A | 11/1996 | Kneeland |
| 5,630,426 A | 5/1997 | Eggers et al. |
| 5,678,565 A | 10/1997 | Sarvazyan |
| 5,699,804 A | 12/1997 | Rattner |
| 5,704,355 A | 1/1998 | Bridges |
| 5,727,569 A | 3/1998 | Benetti et al. |
| 5,735,278 A | 4/1998 | Hoult et al. |
| 5,744,971 A | 4/1998 | Chan et al. |
| 5,758,646 A | 6/1998 | Van Der Meulen et al. |
| 5,800,350 A | 9/1998 | Coppleson et al. |
| 5,807,257 A | 9/1998 | Bridges |
| 5,810,742 A | 9/1998 | Pearlman |
| 5,821,410 A | 10/1998 | Xiang et al. |
| 5,829,437 A | 11/1998 | Bridges et al. |
| 5,830,145 A | 11/1998 | Tenhoff |
| 5,851,180 A | 12/1998 | Crosby et al. |
| 5,884,239 A | 3/1999 | Romanik, Jr. |
| 5,900,618 A | 5/1999 | Anlage et al. |
| 5,927,284 A | 7/1999 | Borst et al. |
| 6,004,263 A | 12/1999 | Nakaichi et al. |
| 6,010,455 A * | 1/2000 | Barnett et al. ............... 600/549 |
| 6,026,323 A | 2/2000 | Skladnev et al. |
| 6,055,451 A | 4/2000 | Bambot et al. |
| 6,055,452 A | 4/2000 | Pearlman |
| 6,061,589 A | 5/2000 | Bridges et al. |
| 6,071,239 A | 6/2000 | Cribbs et al. |
| 6,081,738 A | 6/2000 | Hinohara et al. |
| 6,086,534 A | 7/2000 | Kesten |
| 6,090,041 A | 7/2000 | Clark et al. |
| 6,093,150 A | 7/2000 | Chandler et al. |
| 6,109,270 A | 8/2000 | Mah et al. |
| 6,135,968 A | 10/2000 | Brounstein |
| 6,167,297 A | 12/2000 | Benaron |
| 6,173,604 B1 | 1/2001 | Xiang et al. |
| 6,174,307 B1 | 1/2001 | Daniel et al. |
| 6,203,533 B1 | 3/2001 | Ouchi |
| 6,233,479 B1 | 5/2001 | Haddad et al. |
| 6,258,576 B1 | 7/2001 | Richards-Kortum et al. |
| 6,280,704 B1 | 8/2001 | Schutt et al. |
| 6,287,302 B1 | 9/2001 | Berube |
| 6,308,097 B1 | 10/2001 | Pearlman |
| 6,311,692 B1 | 11/2001 | Vaska et al. |
| 6,315,981 B1 | 11/2001 | Unger |
| 6,321,106 B1 | 11/2001 | Lemelson |
| 6,331,166 B1 | 12/2001 | Burbnk et al. |
| 6,370,426 B1 | 4/2002 | Campbell et al. |
| 6,375,634 B1 | 4/2002 | Carroll |
| 6,377,841 B1 | 4/2002 | Lin et al. |
| 6,380,747 B1 | 4/2002 | Goldfine et al. |
| 6,397,095 B1 | 5/2002 | Eyuboglu et al. |
| 6,405,733 B1 | 6/2002 | Fogarty et al. |
| 6,411,103 B1 | 6/2002 | Tobias et al. |
| 6,500,112 B1 | 12/2002 | Khouri |
| 6,530,944 B2 | 3/2003 | West et al. |
| 6,544,185 B2 | 4/2003 | Montegrande |
| 6,546,787 B1 | 4/2003 | Schiller et al. |
| 6,564,806 B1 | 5/2003 | Fogarty et al. |
| 6,592,520 B1 | 7/2003 | Peszynski et al. |
| 6,597,185 B1 | 7/2003 | Talanov et al. |
| 6,671,540 B1 | 12/2003 | Hochman |
| 6,677,755 B2 | 1/2004 | Belt et al. |
| 6,689,073 B2 | 2/2004 | Quay |
| 6,695,782 B2 | 2/2004 | Ranucci et al. |
| 6,699,206 B2 | 3/2004 | Burbank et al. |
| 6,722,371 B1 | 4/2004 | Fogarty et al. |
| 6,728,565 B2 | 4/2004 | Wendlandt |
| 6,741,077 B2 | 5/2004 | Yokoyama et al. |
| 6,747,454 B2 | 6/2004 | Belt |
| 6,752,154 B2 | 6/2004 | Fogarty et al. |
| 6,766,185 B2 | 7/2004 | Scott |
| 6,813,515 B2 | 11/2004 | Hashimshony |
| 6,064,081 A1 | 1/2005 | Hashimshony |
| 6,840,948 B2 | 1/2005 | Albrecht et al. |
| 6,909,084 B2 | 6/2005 | Tachi et al. |
| 6,936,003 B2 | 8/2005 | Iddan |
| 6,962,587 B2 | 11/2005 | Johnson et al. |
| 7,082,325 B2 | 7/2006 | Hashimshony et al. |
| 7,184,824 B2 | 2/2007 | Hashimshony |
| 7,505,811 B2 | 3/2009 | Hashimshony |
| 7,720,532 B2 | 5/2010 | Hashimshony et al. |
| 7,809,425 B2 | 10/2010 | Hashimshony et al. |
| 7,899,515 B2 | 3/2011 | Hashimshony et al. |
| 7,904,145 B2 | 3/2011 | Hashimshony et al. |
| 8,019,411 B2 | 9/2011 | Hashimshony et al. |
| 8,032,211 B2 | 10/2011 | Hashimshony et al. |
| 2001/0047135 A1 | 11/2001 | Daniels et al. |
| 2001/0051774 A1 | 12/2001 | Littrup et al. |
| 2002/0055754 A1 | 5/2002 | Ranucci et al. |
| 2002/0059938 A1 | 5/2002 | Fogarty et al. |
| 2002/0068880 A1 | 6/2002 | Burbank et al. |
| 2002/0072676 A1 | 6/2002 | Afanassieva |
| 2002/0120265 A1 | 8/2002 | Fowler |
| 2002/0148277 A1 | 10/2002 | Umeda |
| 2003/0036674 A1 | 2/2003 | Bouton |
| 2003/0045798 A1 | 3/2003 | Hular et al. |
| 2003/0062897 A1 | 4/2003 | Belt et al. |
| 2003/0117140 A1 | 6/2003 | Belt et al. |
| 2003/0138378 A1 | 7/2003 | Hashimshony |
| 2003/0146814 A1 | 8/2003 | Wiltshire |
| 2003/0163037 A1 | 8/2003 | Bladen et al. |
| 2003/0171664 A1 | 9/2003 | Wendlandt |
| 2003/0187347 A1 | 10/2003 | Nevo et al. |
| 2003/0187366 A1 | 10/2003 | Hashimshony |
| 2003/0199753 A1 | 10/2003 | Hibner et al. |
| 2003/0216648 A1 | 11/2003 | Lizzi et al. |
| 2003/0229343 A1 | 12/2003 | Albrecht et al. |
| 2004/0065158 A1 | 4/2004 | Schrepfer et al. |
| 2004/0168692 A1 | 9/2004 | Fogarty et al. |
| 2004/0254457 A1 | 12/2004 | Van der Weide |
| 2005/0010131 A1 | 1/2005 | Burbank et al. |
| 2005/0021019 A1 | 1/2005 | Hashimshony et al. |
| 2005/0107717 A1 | 5/2005 | Yamamoto et al. |
| 2005/0119648 A1 | 6/2005 | Swanson |
| 2005/0159689 A1 | 7/2005 | Olson |
| 2006/0253107 A1 | 11/2006 | Hashimshony et al. |
| 2006/0264738 A1 | 11/2006 | Hashimshony et al. |
| 2007/0032739 A1 | 2/2007 | Hashimshony et al. |
| 2007/0032747 A1 | 2/2007 | Hashimshony et al. |
| 2007/0092059 A1 | 4/2007 | Eberhard et al. |
| 2007/0179397 A1 | 8/2007 | Hashimshony et al. |
| 2007/0255169 A1 | 11/2007 | Hashimshony et al. |
| 2007/0260156 A1 | 11/2007 | Hashimshony |
| 2008/0021343 A1 | 1/2008 | Hashimshony et al. |
| 2008/0039742 A1 | 2/2008 | Hashimshony et al. |
| 2008/0154090 A1 | 6/2008 | Hashimshony |
| 2008/0287750 A1 | 11/2008 | Hashimshony et al. |
| 2009/0062637 A1 | 3/2009 | Hashimshony et al. |
| 2012/0123244 A1 | 5/2012 | Hashimshony et al. |

FOREIGN PATENT DOCUMENTS

| | | |
|---|---|---|
| EP | 419235 | 3/1991 |
| GB | 01153980 | 3/1968 |
| JP | 03-041930 | 2/1991 |
| JP | 05-068666 | 3/1993 |
| JP | 06-296578 | 10/1994 |
| JP | 09-243576 | 9/1997 |
| JP | 10-234734 | 9/1998 |
| JP | 2004-016556 | 1/2004 |
| JP | 2004-261344 | 9/2004 |
| JP | 2005-130969 | 5/2005 |
| JP | 2007-159965 | 6/2007 |
| WO | WO 97/12553 | 4/1997 |
| WO | WO 01/42807 | 6/2001 |
| WO | WO 01/43630 | 6/2001 |
| WO | WO 01/65240 | 7/2001 |
| WO | WO 01/62141 | 8/2001 |

(56) References Cited

FOREIGN PATENT DOCUMENTS

| WO | WO 02/32335 | 4/2002 |
|---|---|---|
| WO | WO 02/38032 | 5/2002 |
| WO | WO 02/058531 | 8/2002 |
| WO | WO 03/009752 | 2/2003 |
| WO | WO 03/060462 | 7/2003 |
| WO | WO 2005/009200 | 2/2005 |
| WO | WO 2005/089065 | 9/2005 |
| WO | WO 2006/072947 | 7/2006 |
| WO | WO 2006/092797 | 9/2006 |
| WO | WO 2006/103665 | 10/2006 |
| WO | WO 2007/015255 | 2/2007 |
| WO | WO 2007/083310 | 7/2007 |
| WO | WO 2008/132714 | 11/2008 |
| WO | WO 2008/132750 | 11/2008 |

OTHER PUBLICATIONS

Brown "A Survey of Image Registration Techniques", ACM Computing Surveys, 24(4): 325-376, 1992.
Misra et al. "Noninvasive Electrical Characterization of Materials at Microwave Frequencies Using an Open-Ended Coaxial Line: Test of an Improved Calibration Technique", IEEE Transactions on Microwave Theory & Techniques, 38(1): 8-13, 1990.
Burdette et al. "In Vivo Probe Measurement Technique for Determining Dielectric Properties at VFW Through Microwave Frequencies", IEEE Transactions on Microwave Theory & Techniques, MTT-28(4): 414-427, 1980.
Xu et al. "Measurement of Microwave Permittivity Using Open Ended Elliptical Coaxial Probes", IEEE Transactions on Microwave Theory & Techniques, 40(1): 143-150, 1992.
Stuchly et al. "Measurement of Radio Frequency Permittivity of Biological Tissues With an Open-Ended Coaxial Line: Part II—Experimental Results", IEEE Transactions on Microwave Theory & Techniques, MTT-30(1): 87-91, 1982.
Mosig et al. "Reflection of an Open-Ended Coaxial Line", IEEE Transactions on Instrumentation & Measurement, IM-30(1): 46-51, 1981.
Schwan "Mechanism Responsible for Electrical Properties of Tissues and Cell Suspensions"; Medical Process Through Technology, 19: 163-165, 1993.
Communication Pursuant to Article 94(3) EPC Dated Oct. 7, 2009 From the European Patent Office Re.: Application No. 06728196.4.
International Preliminary Report on Patentability Dated Nov. 12, 2009 From the International Bureau of WIPO Re.: Application No. PCT/IL2008/000406.
Official Action Dated Aug. 27, 2009 From the US Patent and Trademark Office Re.: U.S. Appl. No. 11/705,143.
Official Action Dated Aug. 27, 2009 From the US Patent and Trademark Office Re.: U.S. Appl. No. 11/797,167.
Official Action Dated Oct. 27, 2009 From the US Patent and Trademark Office Re.: U.S. Appl. No. 11/487,431.
Official Action Dated Aug. 31, 2009 From the US Patent and Trademark Office Re.: U.S. Appl. No. 11/797,166.
Response Dated Oct. 13, 2009 to Official Action of Dec. 18, 2008 From the US Patent and Trademark Office Re.: U.S. Appl. No. 10/534,544.
Response Dated Nov. 25, 2009 to Official Action of Aug. 27, 2009 From the US Patent and Trademark Office Re.: U.S. Appl. No. 11/705,143.
Response Dated Nov. 25, 2009 to Official Action of Aug. 27, 2009 From the US Patent and Trademark Office Re.: U.S. Appl. No. 11/797,167.
Supplementary Partial European Search Report and the European Searching Opinion Dated Dec. 4, 2009 From the European Patent Office Re.: Application No. 06700052.1.
Translation of Office Action Dated Sep. 18, 2009 From the State Intellectual Property Office of the People's Republic of China Re.: Application No. 200680006513.7.
Examination Report Dated Feb. 1, 2008 From the Goverment of India, Patent Office Re.: Application No. 668/CHENP/2006.
Examination Report Dated Nov. 18, 2008 From the Government of India, Patent Office Re.: Application No. 668/CHENP/2006.
International Search Report Dated Nov. 27, 2008 From the International Searching Authority Re.: Application No. PCT/IL2008/000406.
Translation of the Office Action Dated Jul. 27, 2007 From the Patent Office of the People's Republic of China Re.: Application No. 200480027097.X.
Written Opinion Dated Nov. 27, 2008 From the International Searching Authority Re.: Application No. PCT/IL2008/000406.
Smith et al. "In Vivo Measurement of Tumor Conductiveness With the Magnetic Bioimpedance Method", IEEE Transactions on Biomedical Engineering, 47(10): 1403-1405, 2000.
Surowiec et al. "Dielectric Properties of Breast Carcinoma and the Surrounding Tissues", IEEE Transactions on Biomedical Engineering, 35(4): 257-263, 1988.
Communication Pursuant to Article 96(2) EPC Dated Aug. 10, 2006 From the European Patent Office Re.: Application No. 02795418.9.
Communication Pursuant to Article 96(2) EPC Dated Jan. 12, 2006 From the European Patent Office Re.: Application No. 02795418.9.
International Preliminary Report on Patentability Dated Feb. 4, 2008 From the International Preliminary Examining Authority Re.: Application No. PCT/IL06/00392.
International Preliminary Report on Patentability Dated Jan. 22, 2009 From the International Bureau of WIPO Re.: Application No. PCT/IL2006/000908.
International Preliminary Report on Patentability Dated Apr. 26, 2007 From the International Bureau of WIPO Re.: Application No. PCT/IL2005/000330.
International Preliminary Report on Patentatbility Dated Aug. 9, 2007 From the International Bureau of WIPO Re.: Applicaiton No. PCT/IL2006/000015.
Office Action Dated Feb. 11, 2009 From the Israeli Patent Office Re.: Application No. 173231 and Its Translation Into English.
Office Action Dated Nov. 18, 2008 From the Government of India, Patent Office Re.: Application No. 668/CHENP/2006.
Office Action Dated Mar. 20, 2009 From the State Intellectual Property Office of the People's Republic of China Re.: Application No. 200680019026.4.
Official Action Dated Apr. 1, 2008 From US Patent and Trademark Office Re.: U.S. Appl. No. 11/745,334.
Official Action Dated Jun. 3, 2005 From the US Patent and Trademark Office Re.: U.S. Appl. No. 10/891,750.
Official Action Dated Jun. 4, 2007 From the US Patent and Trademark Office Re.: U.S. Appl. No. 10/298,196.
Official Action Dated Apr. 10, 2006 From the US Patent and Trademark Office Re.: U.S. Appl. No. 10/965,752.
Official Action Dated Feb. 10, 2006 From the US Patent and Trademark Office Re.: U.S. Appl. No. 10/298,196.
Official Action Dated Oct. 10, 2006 From the US Patent and Trademark Office Re.: U.S. Appl. No. 10/298,196.
Official Action Dated Mar. 21, 2008 From the US Patent and Trademark Office Re.: U.S. Appl. No. 10/558,831.
Official Action Dated Jan. 24, 2008 From the US Patent and Trademark Office Re.: U.S. Appl. No. 10/298,196.
Response Dated Jan. 4, 2007 to Communication Pursuant to Article 96(2) of Aug. 10, 2006 From the European Patent Office Re.: Application No. 02795418.9.
Supplementary European Search Report and the European Search Opinion Dated Jun. 5, 2009 From the European Patent Office Re.: Application No. 06728196.4.
Partial International Search Dated Sep. 1, 2008 From the International Searching Authority Re.: Application No. PCT/IL2008/000406.
Examination Report Dated Feb. 1, 2008 From the Government of India, Patent Office Re.: Application No. 668/CHENP/2006.
International Search Report and the Written Opinion Dated May 3, 2007 From the International Searching Authority Re.: Application No. PCT/IL06/00392.
International Search Report and the Written Opinion Dated Feb. 5, 2007 From the International Searching Authority Re.: Application No. PCT/IL05/00330.

(56) References Cited

OTHER PUBLICATIONS

International Search Report and the Written Opinion Dated Jun. 22, 2005 From the International Searching Authority Re.: Application No. PCT/IL04/00641.
Notice of Allowance Dated Jun. 29, 2010 From the US Patent and Trademark Office Re.: U.S. Appl. No. 11/487,431.
Notification to Grant Patent Right for Invention Dated Aug. 3, 2010 From the State Intellectual Property Office of the People's Republic of China Re.: Application No. 200680019026.4 and Its Translation Into English.
Official Action Dated Jul. 9, 2008 From the US Patent and Trademark Office Re.: U.S. Appl. No. 11/196,732.
Official Action Dated Jul. 9, 2010 From the US Patent and Trademark Office Re.: U.S. Appl. No. 11/705,143.
Official Action Dated Nov. 19, 2007 From the US Patent and Trademark Office Re.: U.S. Appl. No. 11/196,732.
Response Dated Mar. 1, 2010 to Official Action of Oct. 27, 2009 From the US Patent and Trademark Office Re.: U.S. Appl. No. 11/487,431.
Response Dated Mar. 16, 2007 to Communication Pursuant to Article 96(2) EPC of Jan. 19, 2007 From the European Patent Office Re.: Application No. 02795418.9.
Response Dated Sep. 16, 2010 to Official Action of Mar. 16, 2010 From the US Patent and Trademark Office Re.: U.S. Appl. No. 11/887,571.
Supplementary European Search Report Dated Feb. 17, 2005 From the European Patent Office Re.: Application No. 02795418.9.
Official Action Dated Aug. 31, 2010 From the US Patent and Trademark Office Re. U.S. Appl. No. 11/350,102.
Translation of Notice of Reason for Rejection Dated Aug. 24, 2010 From the Japanese Patent Office Re. Application No. 2006-520980.
Translation of Notification to Grant Patent Right for Invention Dated Aug. 3, 2010 From the State Intellectual Property Office of the People's Republic of China Re.: Application No. 200680019026.4.
Communication Pursuant to Article 94(3) EPC Dated Mar. 15, 2010 From the European Patent Office Re.: Application No. 06700052.1.
Communication Relating to the Results of the Partial International Search Dated Sep. 1, 2008 From the International Searching Authority Re.: Application No. PCT/IL2008/000406.
Notice of Allowance Dated Oct. 20, 2006 From the US Patent and Trademark Office Re.: U.S. Appl. No. 10/965,752.
Official Action Dated Mar. 11, 2010 From the US Patent and Trademark Office Re.: U.S. Appl. No. 11/797,166.
Official Action Dated Mar. 16, 2010 From the US Patent and Trademark Office Re.: U.S. Appl. No. 11/887,571.
Official Action Dated Mar. 17, 1010 From the US Patent and Trademark Office Re.: U.S. Appl. No. 10/567,581.
Response Dated Aug. 3, 2007 to Written Opinion of May 3, 2007 From the International Searching Authority Re.: Application No. PCT/IL06/00392.
Response Dated Jan. 3, 2010 to Office Action of Sep. 18, 2009 From the State Intellectual Property Office of the People's Republic of China Re.: Application No. 200680006513.7.
Response Dated Jan. 7, 2010 to Official Action of Dec. 7, 2009 From the US Patent and Trademark Office Re.: U.S. Appl. No. 11/797,167.
Response Dated Feb. 8 2010 to Communication Pursuant to Article 94(3) EPC of Oct. 7, 2009 From the European Patent Office Re.: Application No. 06728196.4.
Response Dated Dec. 30, 2009 to Official Action of Aug. 31, 2009 From the US Patent and Trademark Office Re.: U.S. Appl. No. 11/797,166.
Response Dated Sep. 29, 2010 to Official Action of Aug. 31, 2010 From the US Patent and Trademark Office Re. U.S. Appl. No. 11/350,102.
Communication Pursuant to Article 94(3) EPC Dated Sep. 27, 2010 From the European Patent Office Re.: Application No. 06728196.4.
Response Dated Sep. 16, 2010 to Official Action of Mar. 17, 1010 From the US Patent and Trademark Office Re.: U.S. Appl. No. 10/567,581.

Official Action Dated Sep. 29, 2010 From the US Patent and Trademark Office Re.: U.S. Appl. No. 11/797,167.
Response Dated Sep. 2, 2010 to Communication Pursuant to Article 94(3) EPC of Mar. 15, 2010 From the European Patent Office Re.: Application No. 06700052.1.
Response Dated Aug. 30, 2010 to Official Action of Mar. 11, 2010 From the US Patent and Trademark Office Re.: U.S. Appl. No. 11/797,166.
Translation of Notice of Reason for Rejection Dated Feb. 15, 2011 From the Japanese Patent Office Re. Application No. 2006-520980.
Response Dated Mar. 29, 2011 to Official Action of Sep. 29, 2010 From the US Patent and Trademark Office Re.: U.S. Appl. No. 11/797,167.
Response Dated Mar. 28, 2011 to Communication Pursuant to Article 94(3) EPC of Sep. 27, 2010 From the European Patent Office Re.: Application No. 06728196.4.
Response Dated Apr. 28, 2011 to Official Action of Oct. 28, 2010 From the US Patent and Trademark Office Re.: U.S. Appl. No. 11/797,166.
Notice of Allowance Dated May 17, 2011 From the US Patent and Trademark Office Re.: U.S. Appl. No. 11/705,143.
Response Dated May 30, 2011 to Communication Pursuant to Article 94(3) EPC of Feb. 1, 2011 From the European Patent Office Re.: Application No. 06700052.1.
Translation of Notice of Reason for Rejection Dated Jul. 12, 2011 From the Japanese Patent Office Re. Application No. 2008-503679.
Official Action Dated Jul. 8, 2011 From the US Patent and Trademark Office Re.: U.S. Appl. No. 11/797,166.
Translation of Office Action Dated Jun. 30, 2011 From the State Intellectual Property Office of the People's Republic of China Re.: Application No. 200680006513.7.
Official Action Dated Nov. 23, 2010 From the US Patent and Trademark Office Re.: U.S. Appl. No. 10/567,581.
Response Dated Jun. 13, 2011 to Official Action of Jan. 6, 2011 From the US Patent and Trademark Office Re. U.S. Appl. No. 11/350,102.
Response Dated May 23, 2011 to Official Action of Nov. 23, 2010 From the US Patent and Trademark Office Re.: U.S. Appl. No. 10/567,581.
Official Action Dated Oct. 28, 2010 From the US Patent and Trademark Office Re.: U.S. Appl. No. 11/797,166.
Communication Pursuant to Article 94(3) EPC Dated Feb. 1, 2011 From the European Patent Office Re.: Application No. 06700052.1.
Response Dated Jan. 26, 2011 to Office Action of Aug. 4, 2010 From the State Intellectual Property Office of the People's Republic of China Re. Application No. 200680037103.9.
Translation of Office Action Dated Aug. 4, 2010 From the State Intellectual Property Office of the People's Republic of China Re. Application No. 200680037103.9.
Response Dated Jan. 16, 2011 to Notice of Reason for Rejection of Aug. 24, 2010 From the Japanese Patent Office Re. Application No. 2006-520980.
Official Action Dated Jan. 6, 2011 From the US Patent and Trademark Office Re. U.S. Appl. No. 11/350,102.
Response Dated Dec. 27, 2010 to Official Action of Jul. 9, 2010 From the US Patent and Trademark Office Re.: U.S. Appl. No. 11/705,143.
Communication Pursuant to Article 94(3) EPC Dated Jun. 7, 2013 From the European Patent Office Re. Application No. 06700052.1.
Translation of Notice of Reason for Rejection Dated Jun. 5, 2012 From the Japanese Patent Office Re. Application No. 2008-524676.
Requisition by the Examiner Dated Jun. 22, 2012 From the Canadian Intellectual Property Office Re. Application No. 2,603,025.
Requisition by the Examiner Dated Jul. 8, 2013 From the Canadian Intellectual Property Office Re. Application No. 2,616,962.
Translation of Notice of Reason for Rejection Dated Jul. 27, 2012 From the Japanese Patent Office Re. Application No. 2008-503679.
Office Action Dated Sep. 26, 2011 From the State Intellectual Property Office of the People's Republic of China Re. Application No. 20100528113.0 and Its Translation Into English.
Restriction Official Action Dated Jul. 26, 2013 From the US Patent and Trademark Office Re. U.S. Appl. No. 13/337,183.
Translation of Notice of Reason for Rejection Dated Jul. 2, 2013 From the Japanese Patent Office Re. Application No. 2008-524676.

(56) References Cited

OTHER PUBLICATIONS

Translation of Summary of the Reason for Rejecting Your Proposed Claims Dated Aug. 13, 2013 From the Japanese Patent Office Re. Application No. 2007-550012.
Official Action Dated Sep. 10, 2013 From the US Patent and Trademark Office Re. U.S. Appl. No. 10/567,581.
Translation of Notice of Reason for Rejection Dated Oct. 2, 2012 From the Japanese Patent Office Re. Application No. 2007-550012.
Notice of Allowance Dated Sep. 26, 2011 From the US Patent and Trademark Office Re. U.S. Appl. No. 11/350,102.
Official Action Dated Aug. 31, 2011 From the US Patent and Trademark Office Re. : U.S. Appl. No. 10/567,581.
Translation of Notice of Reason for Rejection Dated Aug. 19, 2011 From the Japanese Patent Office Re. Application No. 2007-550012.
Translation of Office Action Dated Sep. 26, 2011 From the State Intellectual Property Office of the People's Republic of China Re. Application No. 20100528113.0.
Official Action Dated Nov. 20, 2012 From the US Patent and Trademark Office Re. U.S. Appl. No. 12/334,565.
Translation of Office Action Dated Nov. 5, 2012 From the State Intellectual Property Office of the People's Republic of China Re.: Application No. 200680006513.7.
Examiner-Initiated Interview Summary Dated Sep. 23, 2011 From the US Patent and Trademark Office Re. U.S. Appl. No. 11/350,102.
Response Dated Dec. 4, 2011 to Notice of Reason for Rejection of Jul. 12, 2011 From the Japanese Patent Office Re. Application No. 2008-503679.
Translation of Notice of Reason for Rejection Dated Nov. 4, 2011 From the Japanese Patent Office Re. Application No. 2008-524676.
Summons to Attend Oral Proceedings Pursuant to Rule 115(1) EPC Dated Jan. 3, 2013 From the European Patent Office Re. Application No. 06728196.4.
Communication Pursuant to Article 94(3) EPC Dated Feb. 20, 2012 From the European Patent Office Re.: Application No. 06700052.1.
Communication Pursuant to Article 94(3) EPC Dated Feb. 27, 2013 From the European Patent Office Re. Application No. 04744981.4.
Official Action Dated Feb. 28, 2013 From the US Patent and Trademark Office Re. U.S. Appl. No. 12/334,565.
Official Action Dated Mar. 14, 2012 From the US Patent and Trademark Office Re.: U.S. Appl. No. 10/567,581.
Restriction Official Action Dated Mar. 27, 2013 From the US Patent and Trademark Office Re. U.S. Appl. No. 13/337,183.
Translation of Office Action Dated Mar. 12, 2012 From the State Intellectual Property Office of the People's Republic of China Re. Application No. 200680037103.9.
Restriction Official Action Dated Apr. 25, 2012 From the US Patent and Trademark Office Re. U.S. Appl. No. 12/334,565.
Requisition by the Examiner Dated May 24, 2013 From the Canadian Intellectual Property Office Re. Application No. 2,594,427.
Requisition by the Examiner Dated Jan. 9, 2012 From the Canadian Intellectual Property Office Re. Application No. 2,533,161.
Brown et al. "Room Temperature, THz Photomixing Sweep Oscillator and Its Application to Spectroscopic Transmission Through Organic Materials", Review of Scientific Instruments, XP012071969, 75(12): 5333-5342, Nov. 30, 2004. Abstract.
Volakis et al. "A Broadband Cavity-Backes Slot Spiral Antenna", IEEE Antennas and Propagation Magazine, XP011091638, 43(6): 15-26, Dec. 1, 2001.
Translation of Office Action Dated Apr. 24, 2012 From the State Intellectual Property Office of the People's Republic of China Re. Application No. 200680006513.7.
Official Action Dated Dec. 11, 2013 From the US Patent and Trademark Office Re. U.S. Appl. No. 13/337,183.

\* cited by examiner

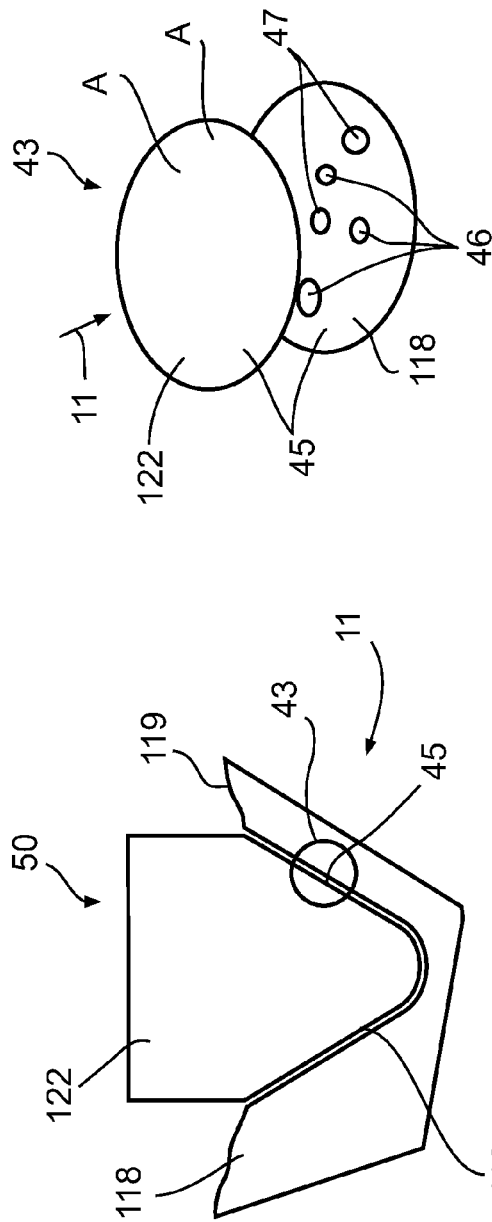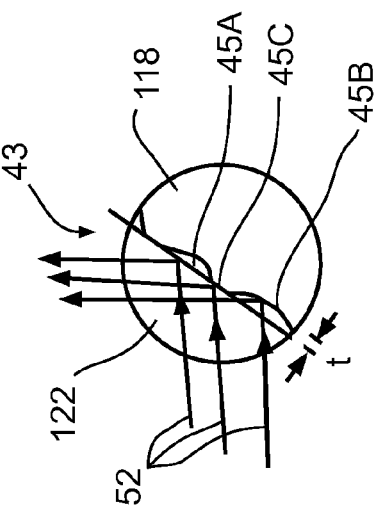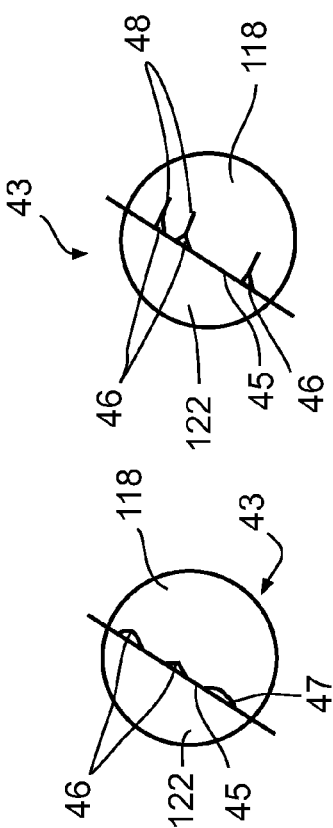

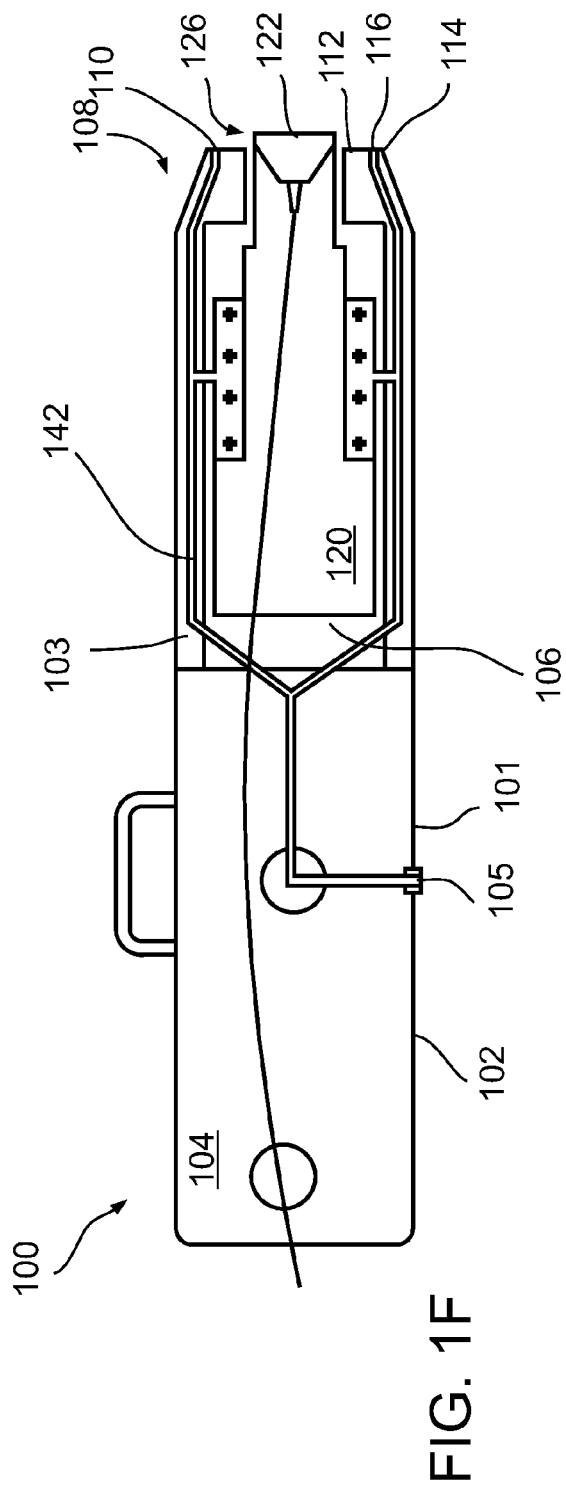
FIG. 1F
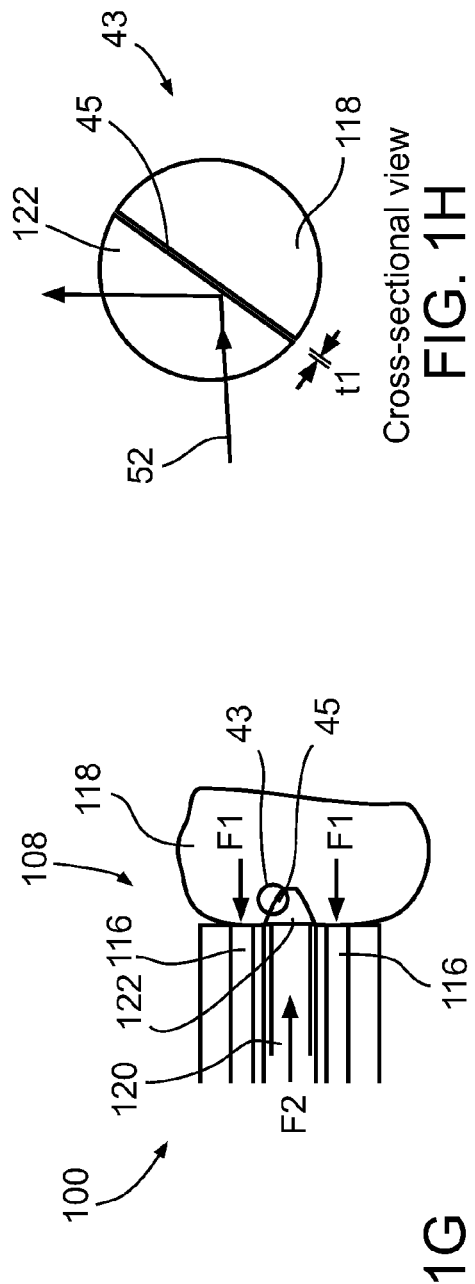
FIG. 1H
FIG. 1G

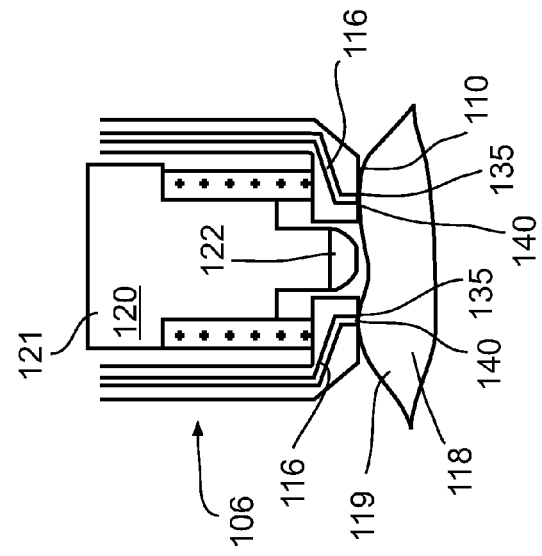
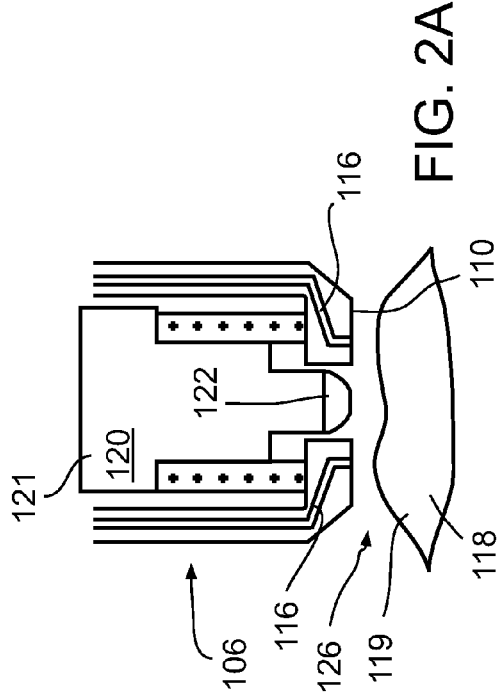
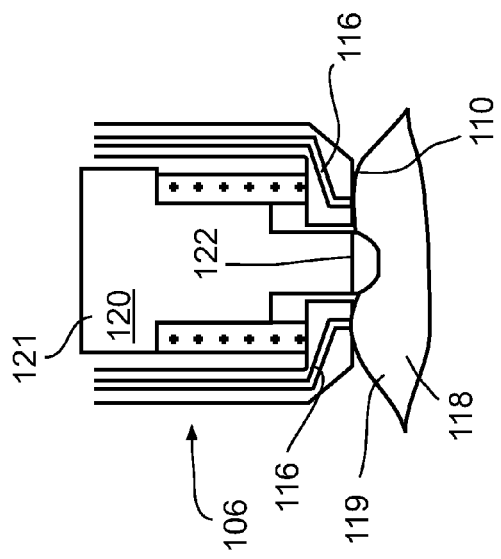
FIG. 2B
FIG. 2A
FIG. 2C

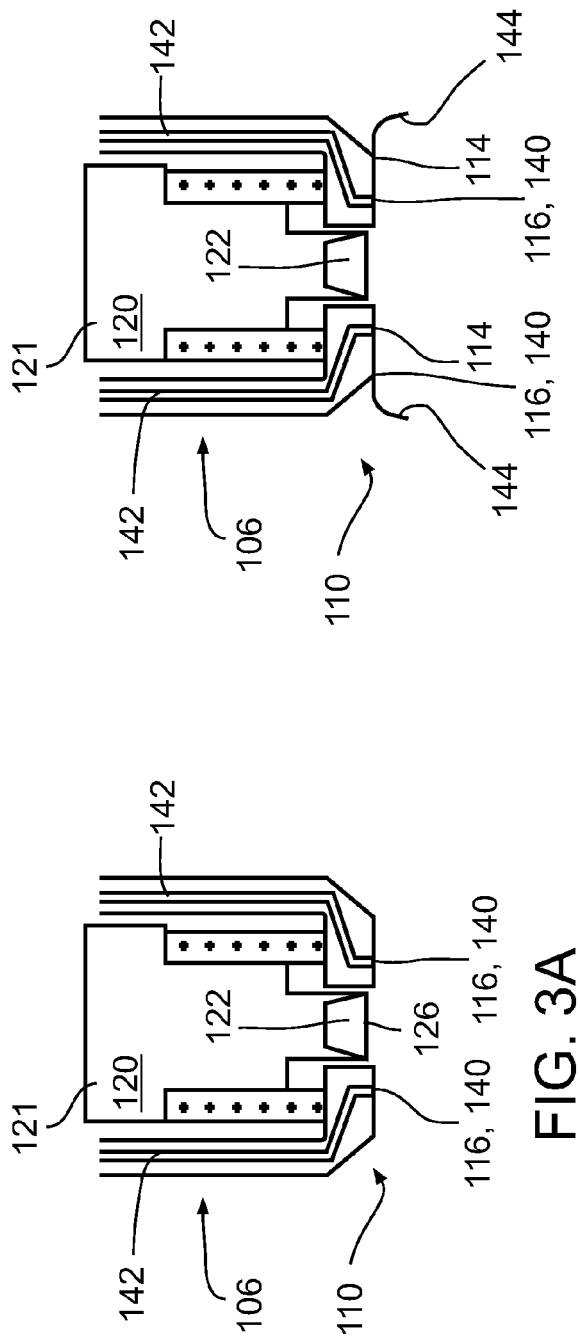
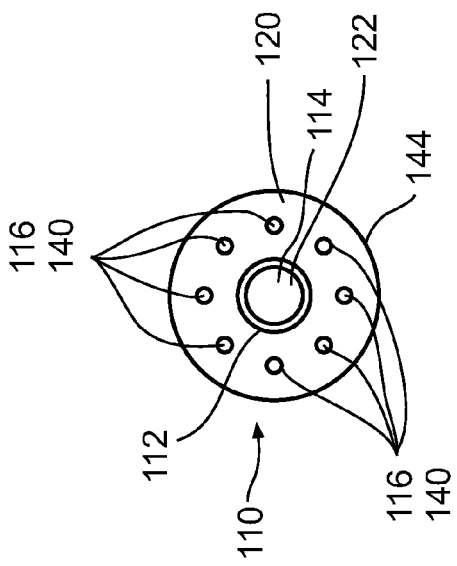

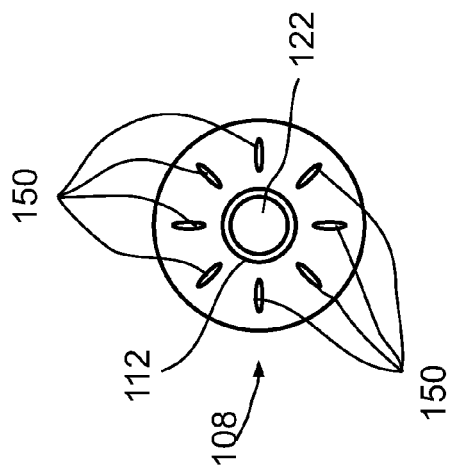
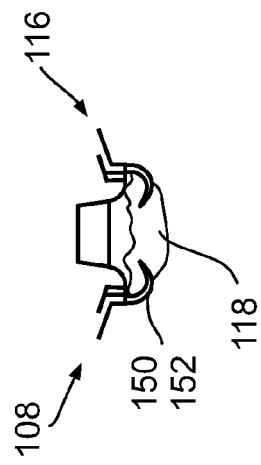
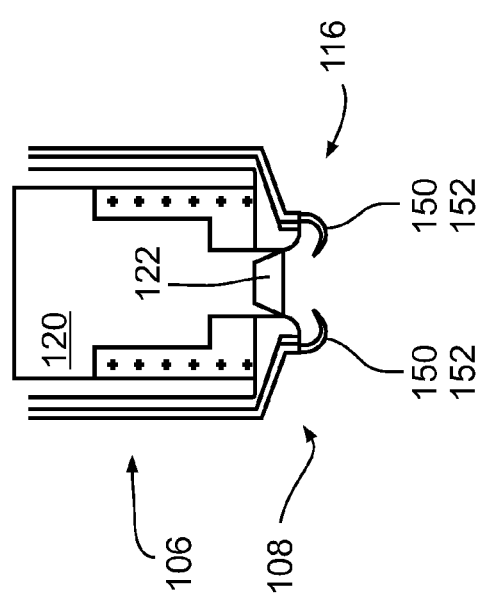
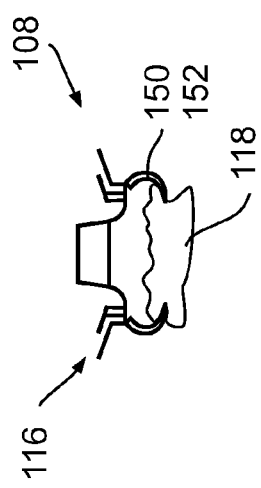

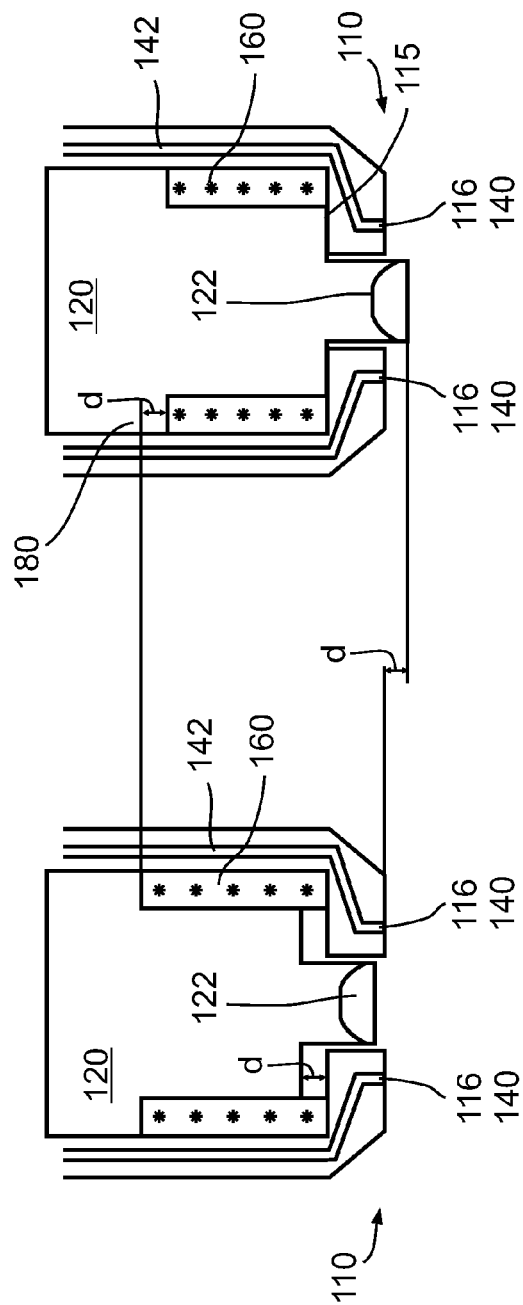

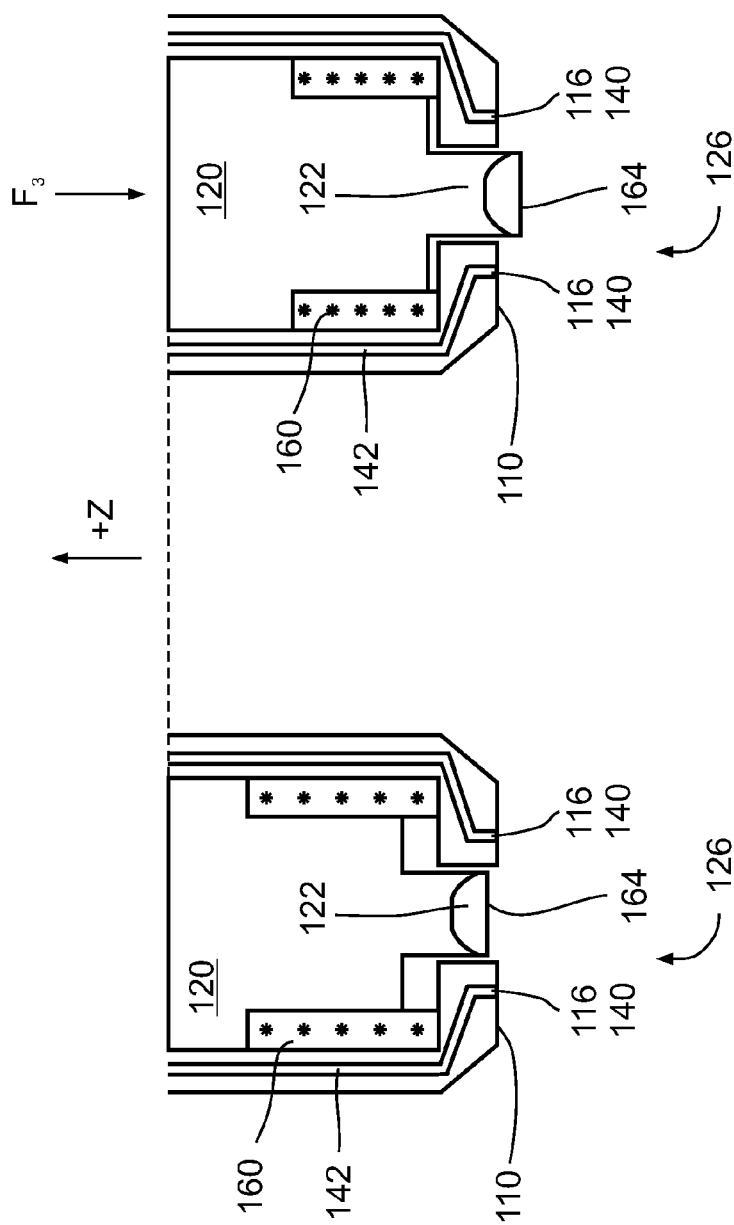

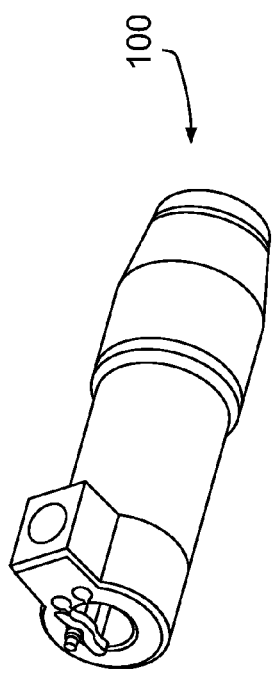
FIG. 10A
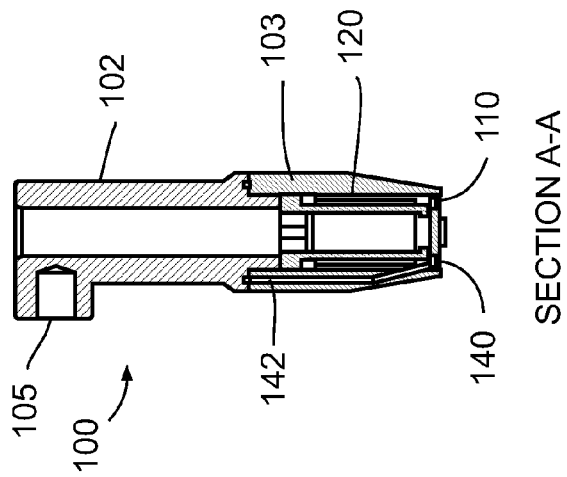
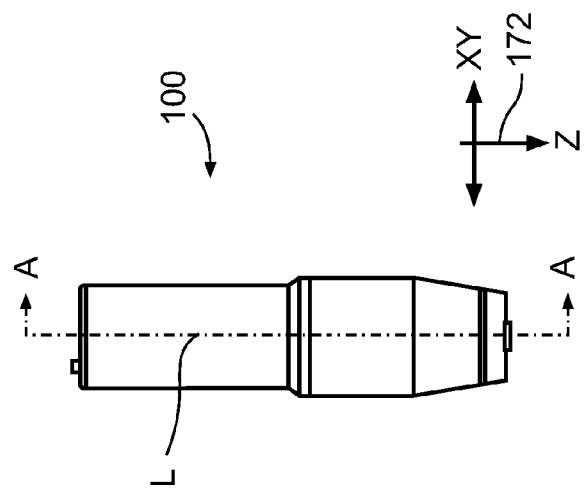
FIG. 10C
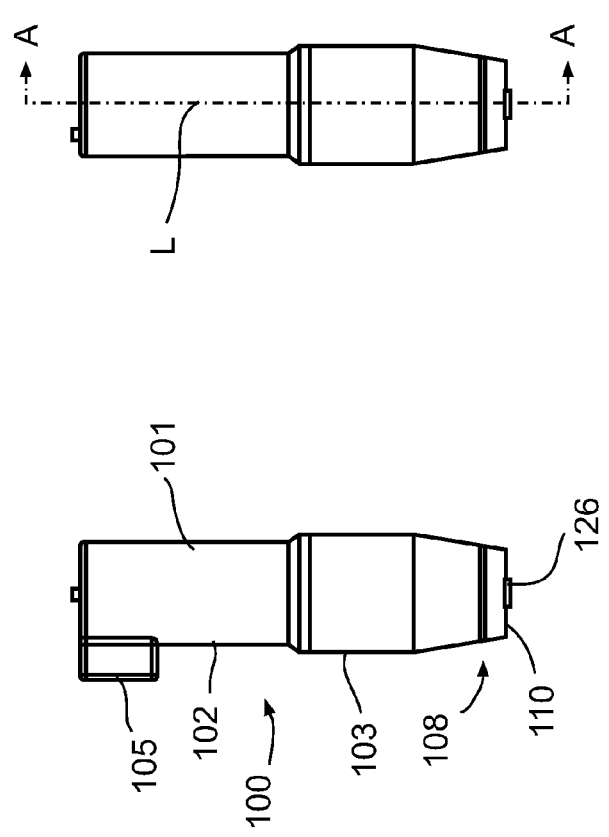
FIG. 10B
FIG. 10D

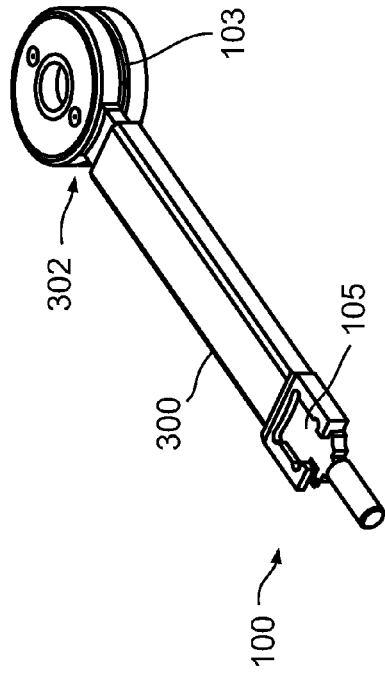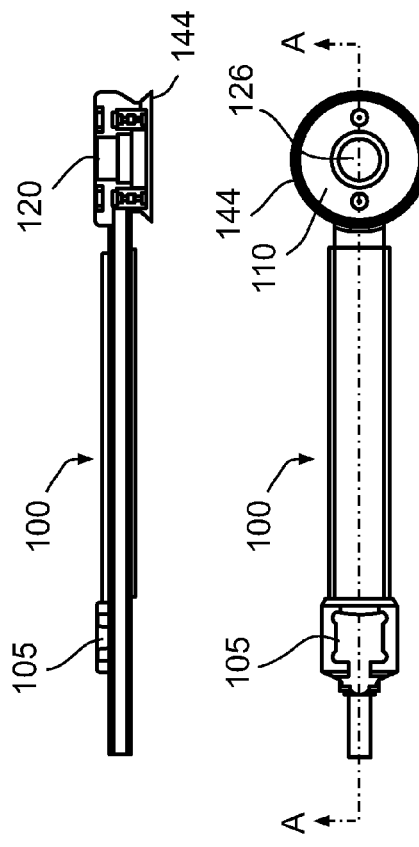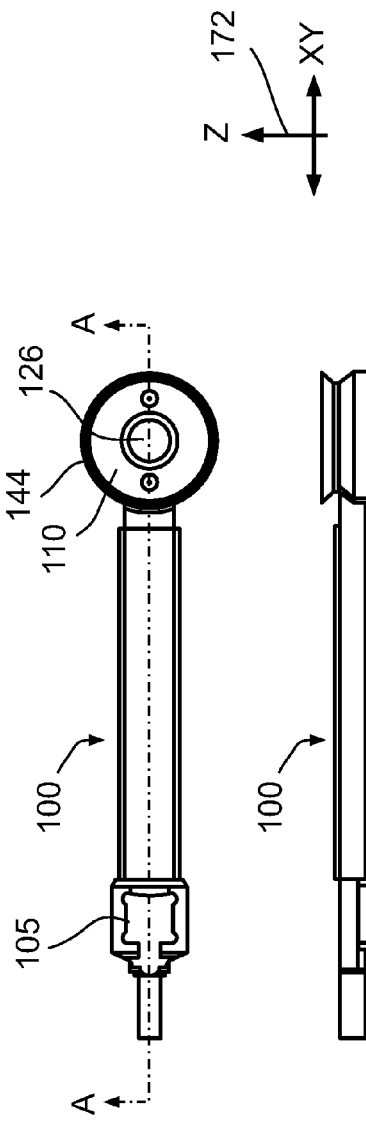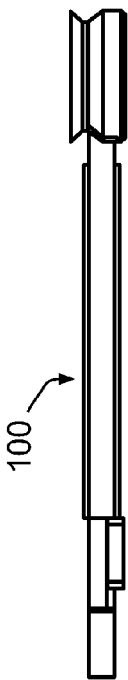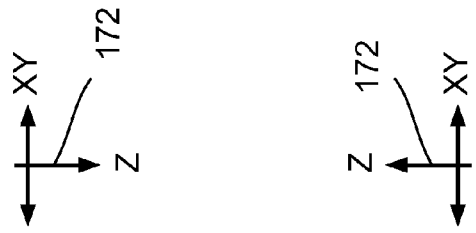
FIG. 11A
FIG. 11B
FIG. 11C
FIG. 11D

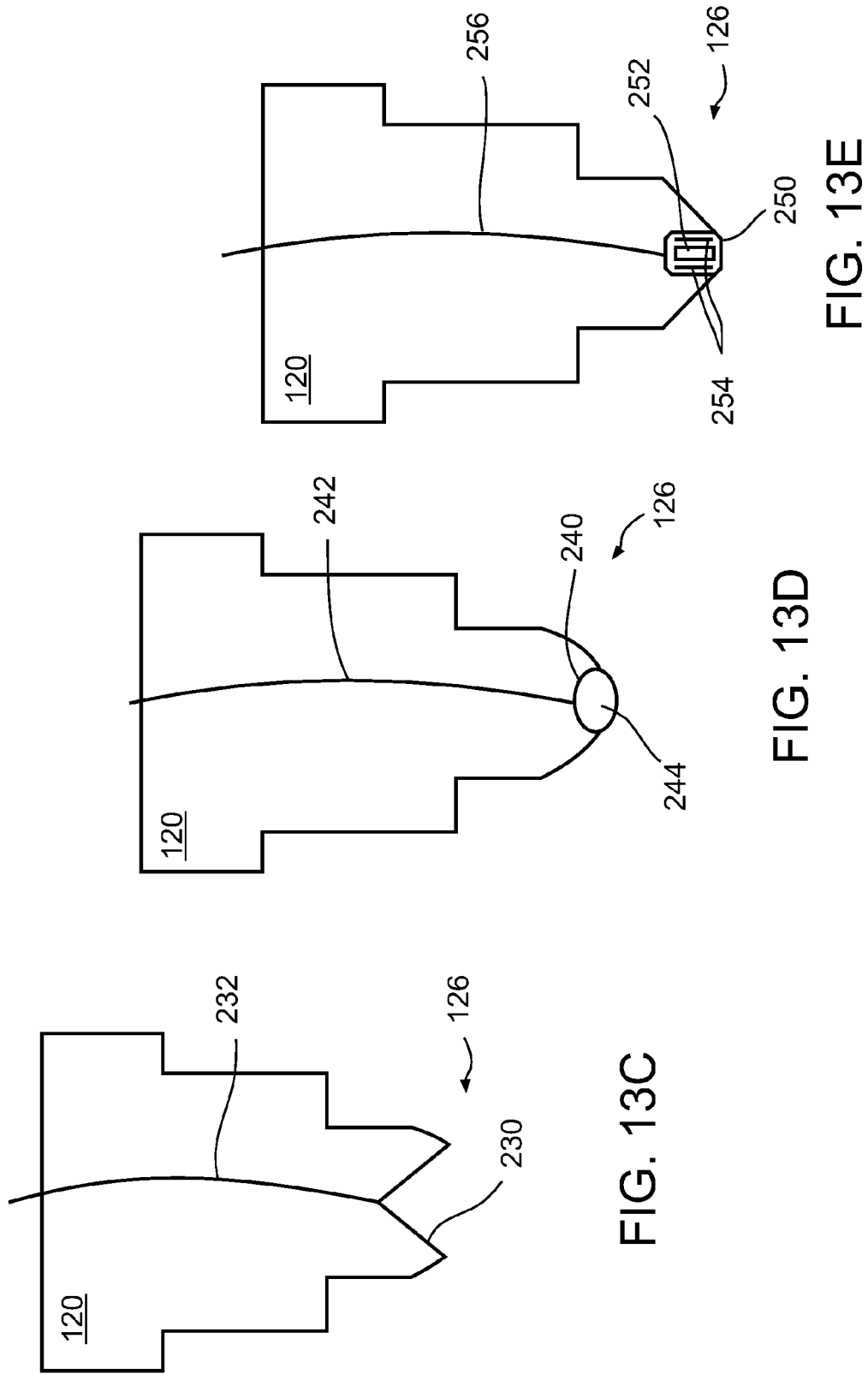

DEVICE FOR FORMING AN EFFECTIVE SENSOR-TO-TISSUE CONTACT

FIELD AND BACKGROUND OF THE INVENTION

The present invention relates generally, to tissue characterization, and specifically, to a device and method for forming effective sensor-to-tissue contact, for tissue characterization.

The use of suction, for engaging a medical instrument to a tissue, is known. For example: U.S. Pat. No. 5,727,569 to Benetti et al., entitled: "Surgical devices for imposing a negative pressure to fix the position of cardiac tissue during surgery", whose disclosure is incorporated herein by reference, teaches devices and techniques of using a negative (suction) pressure or vacuum, applied through surgical instruments for fixing the position of a portion of the surface of a beating heart so that a surgical procedure can be more easily performed. The devices apply negative pressure at several points on the outer surface of the heart such that a portion of the heart is fixed in place by the suction imposed through the surgical instrument. Because the instrument fixes the position of the tissue, and because the instruments remain at a constant distance from the particular portion of the heart where surgery is performed, the device may also serve as a support or platform so that other surgical instruments or devices can be advantageously used at the site. In certain preferred embodiments, the devices described are structured to facilitate the use of additional surgical instruments such that the placement of the negative pressure device permits the surgeon to advantageously manipulate the other instruments during surgery. The negative pressure is preferably imposed through a plurality of ports that may be disposed in a substantially planar surface of the instrument that contacts the cardiac tissue.

In addition, U.S. Pat. No. 5,927,284, to Borst, entitled, "A Method and Apparatus for Temporarily Immobilizing a Local Area of Tissue," whose disclosure is incorporated herein by reference, describes temporarily immobilizing a local area of heart tissue to permit surgery on a coronary vessel in that area without significant deterioration of the pumping function of the beating heart. The local area of heart tissue is immobilized to a degree sufficient to permit minimally invasive or microsurgery on that area of the heart. A suction device is used to accomplish the immobilization. The suction device is coupled to a source of negative pressure. The suction device has a series of suction ports on one surface. Suction through the device causes suction to be maintained at the ports. The device is shaped to conform to the surface of the heart. Thus, when the device is placed on the surface of the heart and suction is created, the suction through the ports engages the surface of the heart. The suction device is further fixed or immobilized to a stationary object, such as an operating table or a sternal or rib retractor. Thus, the local area of the heart near the suction device is temporarily fixed or immobilized relative to the stationary object while suction is maintained. In this fashion, the coronary artery may be immobilized, even though the heart itself is still beating so that a bypass graft may be performed. In addition, the suction device may be used in either a conventional, open-chest environment or in a minimally-invasive, endoscopic environment.

U.S. Pat. No. 6,728,565, to Wendlandt, entitled, "Diagnostic Catheter Using a Vacuum for Tissue Positioning," whose disclosure is incorporated herein by reference, describes the use of a diagnostic catheter, associated with a vacuum source, for attaching a sensor to a tissue surface. The method includes inserting a catheter with a sensor at its distal end into the body of a patient, applying suction through the catheter, to draw tissue into a predetermined sensing position for the sensor, and analyzing the tissue with the sensor. The degree of vacuum may be adjusted, so that only the required amount of force is used to maintain contact between the sensor or sensors and the tissue being analyzed.

U.S. Pat. No. 6,090,041, to Clark, entitled, "Vacuum Actuated Surgical Retractor and Methods," whose disclosure is incorporated herein by reference, describes a surgical retractor for retracting body tissue or organs, using suction. The surgical retractor includes an end piece adapted for sealing engagement with body tissue, the end piece having at least one suction port therein, the at least one suction port operably linked to at least one vacuum line. Suction supplied to the at least one suction port may be controlled by a vacuum control unit. Retractors of the invention may be provided in a range of shapes and sizes, according to the intended application or tissue to be retracted. A method for making a vacuum actuated retractor of the invention is disclosed, together with a method for automatically retracting body tissue.

U.S. Pat. No. 6,695,782 to Ranucci et al., teaches an ultrasonic tissue ablation device comprising a transversely elongated probe and a coupling assembly for probe attachment and detachment that enables the probe assembly and separation from the device body that includes the ultrasound energy source and sound conductor, and a method of use for removal of vascular occlusions in blood vessels. The coupling assembly enables incorporation of elongated probes with small cross sectional lumens such as a catheter guide wire. The probe can be used with acoustic and/or aspiration sheaths to enhance destruction and removal of an occlusion. The horn assembly of the device that contains a sound conducting horn functions as an energy regulator and reservoir for the probe, and precludes loss of probe cavitation energy by its bending or damping within the blood vessel.

U.S. Pat. No. 6,500,112, to Khouri, entitled, "Vacuum dome with supporting rim and rim cushion," whose disclosure is incorporated herein by reference, describes the use of vacuum for tissue stretching, to enlarge a soft tissue, for example after a breast surgery, or to correct a deformity. It utilizes a generally rigid dome, capable of withstanding a pressure differential, with a rim cushion underlying the rim of the dome, for supporting the rim against the patient's skin surface. The rim may be generally wider than the dome in order to distribute the attendant forces across a greater surface and avoid tissue damage. A sticky sole underlies the rim cushion and seals the rim cushion to the patient's skin, to thereby preserve the vacuum within the dome. The sticky sole may be any adhesive material or be achieved through the use of an appropriate material for the rim cushion itself. Unlike the other references, described hereinabove, in U.S. Pat. No. 6,500,112, the vacuum is used for its therapeutic effect, i.e., tissue stretching, to enlarge a soft tissue or to correct a deformity, rather than as means for attaching another instrument.

Different types of sensors and probes for tissue characterizations are known and available today. Even though the operating principles of the different types of tissue characterization techniques differ, effective contact between the sensor and the tissue itself is often essential for reliable results. For example, the presence of air bubbles between an ultrasound tool and the tissue will interfere with ultrasound measurements. Similarly, a liquid layer may interfere with optical spectroscopy. There is thus a recognized need for devices and methods for ensuring effective contact between the sensor and the tissue, free of air, liquid and foreign matter.

SUMMARY OF THE INVENTION

The present invention successfully addresses the shortcoming of the presently known configurations by providing a device and method for tissue characterization, the device comprising: a structure; a first mechanism, associated with said structure, configured for exerting a first force on a tissue, for fixing the tissue to said structure, so as to substantially immobilize the tissue; and a second mechanism, associated with said structure, configured for pressing a sensor against an external surface of the immobilized tissue, thereby exerting a second force on the immobilized tissue, wherein at least a component of said first force is in opposition to at least a component of said second force, forcing the immobilized tissue against said sensor, and forcing said sensor against the immobilized tissue, bringing about an effective contact between said sensor and the immobilized tissue.

In accordance with an aspect of the present invention, there is thus provided a device for tissue characterization, comprising:

a structure;

a first mechanism, associated with the structure, configured for exerting a first force on a tissue, for fixing the tissue to the structure, so as to substantially immobilize the tissue; and a second mechanism, associated with the structure, configured for pressing a sensor against an external surface of the immobilized tissue, thereby exerting a second force on the immobilized tissue, wherein at least a component of the first force is in opposition to at least a component of the second force, forcing the immobilized tissue against the sensor, and forcing the sensor against the immobilized tissue, bringing about an effective contact between the sensor and the immobilized tissue.

In accordance with an additional aspect of the present invention, the effective contact is a contact level of 95%.

In accordance with an additional aspect of the present invention, the effective contact is a contact level of 99%.

In accordance with an additional aspect of the present invention, the effective contact is a contact level of 99.8%.

In accordance with an additional aspect of the present invention, the sensor is a sensor of a wavelength $\lambda$, and an average distance t1, between external-most surfaces of the tissue and the sensor is such that $t1<\lambda/3$.

In accordance with an additional aspect of the present invention, the sensor is a sensor of a wavelength $\lambda$, and an average distance t1, between external-most surfaces of the tissue and the sensor is such that $t1<\lambda/10$.

In accordance with an additional aspect of the present invention, the sensor is a sensor of a wavelength $\lambda$, and an average distance t1, between external-most surfaces of the tissue and the sensor is such that $t1<\lambda/100$.

In accordance with an alternative aspect of the present invention, an average distance t1, between external-most surfaces of the tissue and the sensor, is less than 500 Angstroms.

In accordance with an additional aspect of the present invention, an average distance t1, between external-most surfaces of the tissue and the sensor, is less than 50 Angstroms.

In accordance with an additional aspect of the present invention, an average distance t1, between external-most surfaces of the tissue and the sensor, is less than 5 Angstroms.

In accordance with an additional aspect of the present invention, the first mechanism is a suction source, for fixing and substantially immobilizing the tissue, by suction.

In accordance with an additional aspect of the present invention, the second mechanism is a piston, configured for sliding proximally and distally, and containing the sensor at a proximal end thereof.

In accordance with an additional aspect of the present invention, the piston is further configured for vibrating laterally, as it slides proximally, to provide a gliding-sweeping motion against the tissue.

In accordance with an additional aspect of the present invention, the piston is configured to slide proximally a predetermined distance.

In accordance with an alternative aspect of the present invention, the piston is configured to slide proximally until a predetermined force is reached.

In accordance with an additional aspect of the present invention, wherein the device further comprises a spring, for regulating the second force.

In accordance with an alternative aspect of the present invention, the first mechanism is a gripping device, for gripping the tissue.

In accordance with an additional aspect of the present invention, the sensor is selected from the group consisting of an optical sensor, an MRI sensor, an RF sensor, a MW sensor, an X-ray sensor, an ultrasound sensor, a temperature sensor, an infrared thermography sensor, a biosensor, a chemical sensor, and a mechanical sensor.

In accordance with an aspect of the present invention, there is thus provided a system for tissue characterization, comprising:

a device for tissue characterization, which comprises:
a structure;
a first mechanism, associated with the structure, configured for exerting a first force on a tissue, for fixing the tissue to the structure, so as to substantially immobilize the tissue; and
a second mechanism, associated with the structure, configured for pressing a sensor against an external surface of the immobilized tissue, thereby exerting a second force on the immobilized tissue, wherein at least a component of the first force is in opposition to at least a component of the second force, forcing the immobilized tissue against the sensor, and forcing the sensor against the immobilized tissue, thus bringing about an effective contact between the sensor and the immobilized tissue; and
a signal analyzer, in signal communication with the sensor.

In accordance with an additional aspect of the present invention, wherein the system further comprises a signal generator.

In accordance with an additional aspect of the present invention, wherein the system further comprises a computer, in communication with the signal analyzer.

In accordance with an aspect of the present invention, there is thus provided a method for tissue characterization, comprising:

providing a device for tissue characterization, which comprises:
a structure;
a first mechanism, associated with the structure, configured for exerting a first force on a tissue, for fixing the tissue to the structure, so as to substantially immobilize the tissue; and
a second mechanism, associated with the structure, configured for pressing a sensor against an external surface of the immobilized tissue, thereby exerting a second force on the immobilized tissue,
wherein at least a component of the first force is in opposition to at least a component of the second force, forcing the immobilized tissue against the sensor, and forcing the sensor against the immobilized tissue, thus bringing about an effective contact between the sensor and the immobilized tissue;

fixing the tissue to the structure, thus substantially immobilizing the tissue; and pressing the sensor against the external surface of the immobilized tissue, thereby exerting the second force on the immobilized tissue, wherein at least the component of the first force is in opposition to at least the component of the second force, forcing the immobilized tissue against the sensor, and forcing the sensor against the immobilized tissue, thus bringing about the effective contact between the sensor and the immobilized tissue.

In accordance with an aspect of the present invention, there is thus provided a method of tissue characterization, comprising:

exerting a first force on a tissue, for fixing the tissue to a structure, so as to substantially immobilize the tissue; and pressing a sensor against an external surface of the immobilized tissue, thereby exerting a second force on the immobilized tissue, wherein at least a component of the first force is in opposition to at least a component of the second force, forcing the immobilized tissue against the sensor, and forcing the sensor against the immobilized tissue, thus bringing about an effective contact between the sensor and the immobilized tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1E schematically illustrate poor interfaces between a tissue and a sensor;

FIG. 1F schematically illustrates side cross-sectional views of a device for forming effective sensor-to-tissue contact, according to a preferred embodiment of the present invention;

FIG. 1G schematically illustrates a force diagram for the tissue-sensor interface, in accordance with the present invention;

FIG. 1H schematically illustrates an interface of effective sensor-to-tissue contact, according to the present invention;

FIGS. 2A-2C schematically illustrate the proximal end of a device for forming effective sensor-to-tissue contact, during three time steps in the operation of the device, in accordance with the present invention;

FIGS. 3A-3C schematically illustrate side and top cross-sectional views of a first mechanism for attaching the device to the tissue surface, according to an embodiment of the present invention;

FIGS. 4A-4D schematically illustrate side and top cross-sectional views of the first mechanism for attaching the device to the tissue surface, according to another embodiment of the present invention;

FIGS. 8A-8D schematically illustrate manners of controlling the piston travel, according to two alternative embodiments of the present invention;

FIGS. 10A-10D schematically illustrate a prototype of the device for tissue characterization, in accordance with a preferred embodiment of the present invention;

FIGS. 11A-11D schematically illustrate another prototype of the device for tissue characterization, in accordance with yet another preferred embodiment of the present invention;

FIGS. 13A-13E schematically illustrate types of sensors for use with the device of the present invention.

DESCRIPTION OF THE PREFERRED EMBODIMENTS

Figure 5A:
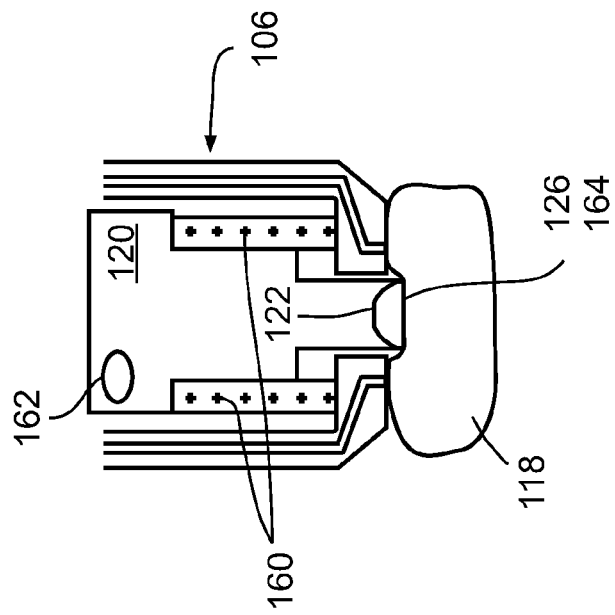
FIGS. 5A-5B schematically illustrate a side cross-sectional view of a second mechanism, for forming effective sensor-to-tissue contact, according to the present invention.

The present invention is of a device and method for tissue characterization, the device comprising: a structure; a first mechanism, associated with said structure, configured for exerting a first force on a tissue, for fixing the tissue to said structure, so as to substantially immobilize the tissue; and a second mechanism, associated with said structure, configured for pressing a sensor against an external surface of the immobilized tissue, thereby exerting a second force on the immobilized tissue, wherein at least a component of said first force is in opposition to at least a component of said second force, forcing the immobilized tissue against said sensor, and forcing said sensor against the immobilized tissue, bringing about an effective contact between said sensor and the immobilized tissue.

The sensor may be an optical sensor, an MRI sensor, an RF sensor, a MW sensor, an X-ray sensor, an ultrasound sensor, a temperature sensor, an infrared thermography sensor, a biosensor, a chemical sensor, and a mechanical sensor, or another sensor, as known.

Before explaining at least one embodiment of the invention in detail, it should be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIGS. 1A-1E, which schematically illustrate poor interface contact between a tissue and a sensor.

FIG. 1A describes a sensor-tissue arrangement 50, and in particular, an interface 45 between a sensor 122 and a tissue 118, along a section 43, of the sensor-tissue arrangement 50. The tissue 118 defines a tissue surface 119.

FIG. 1B provides a cross-sectional view of the interface 45, showing bubbles 46 of air or fluids, and (or) inclusions 47 of foreign matter, which reduce and otherwise deteriorate the quality of the contact area between the tissue 118 and the sensor 122, along the interface 45.

FIG. 1C also provides the cross-sectional view of the interface 45, showing that tissue folds 48, possibly with bubbles 46, may also reduce and otherwise deteriorate the quality of the contact area between the tissue 118 and the sensor 122, along the interface 45.

FIG. 1D provides a view of the interface 45, from the direction of an arrow 11 of FIG. 1A, showing the bubbles 46 and the inclusions 47, reducing an area A of the interface 45.

Defining an overall contact area, A(interface), as the whole area of the interface 45, and defining bubble and inclusions area, A(bubbles and inclusions), as an area covered by bubbles 46 of air and (or) fluid, and (or) covered by inclusions 47 of foreign matter, we may calculate a contact level, as follows:

$$\text{Contact Level} = \frac{A(\text{interface}) - A(\text{bubbles and inclusions})}{A(\text{interface})}$$

In this manner, it is possible to quantify the effect of the bubbles 46 and the inclusions 47, and evaluate if the interface 45 is acceptable for tissue characterization, with a given sensor.

FIG. 1E again provides the cross-sectional view of the interface 45, in reference to irradiative sensors, showing a situation where the external-most surfaces of the tissue 118 and the sensors 122 are slightly apart, by an average distance t, so that in effect, there are three interfaces, 45A, 45B, and 45C, which may operate as three distinct reflective surfaces to radiation 52. The first, 45A, is the edge surface of sensor 122, the second, 45B, is the tissue surface 119, and the third, 45C, is a joint interface of sensor 122 and tissue surface 119, at a point of contact. This effect may be important for radiation of a wavelength λ, for which the average distance t and the radiation wavelength λ are of a same order of magnitude.

Reference is now made to FIGS. 1F-1H, which schematically illustrate the principles of a device 100, for tissue characterization, with effective sensor-to-tissue contact, in accordance with the present invention.

FIG. 1F schematically illustrates a cross-sectional view of a device 100, for forming effective sensor-to-tissue contact, to improve tissue characterization, in accordance with a preferred embodiment of the present invention. Device 100 comprises:

i. a structure 101;

ii. a first mechanism 116, associated with structure 101 and configured for exerting a first force on a tissue 118, for fixing tissue 118 to structure 101, so as to substantially immobilize tissue 118; and iii. a second mechanism 120, associated with structure 101, configured for pressing a sensor 122 against the tissue surface 119 (FIG. 1A) of the immobilized tissue 118, thereby exerting a second force on immobilized tissue 118, wherein a component of the first force is in opposition to a component of the second force, forcing immobilized tissue 118 against sensor 122, and forcing sensor 122 against immobilized tissue 118, bringing about an effective contact between sensor 122 and immobilized tissue 118.

In accordance with the preferred embodiment, structure 101 includes a first portion 102, forming a distal portion 104, adapted for hand gripping, and a second, proximal portion 106, having a proximal end 108, with respect to tissue 118. Proximal end 108 has a frame 110, preferably formed as a ring, of an inner diameter 112 and an outer diameter 114. Frame 110 is associated with first mechanism 116, such as suction, designed for attaching tissue 118 to frame 110.

A duct system 142 provides air-pressure communication between a pump 268 (shown hereinbelow in FIG. 12), and frame 110, for creating a negative pressure required to attach tissue 118 to frame 110, by suction. A vacuum outlet 105 is adapted for connecting to a pump.

Additionally, device 100 includes a second mechanism, such as a piston 120. Piston 120 includes sensor 122, at a proximal end 126.

Piston 120 is selectively configured for deployed and retracted positions. For deployment, it slides proximally and presses against tissue 118, while it is held fast by first mechanism 116, thus achieving effective sensor-to-tissue contact between sensor 122 and tissue 118.

FIG. 1G schematically illustrates a balance of force diagram of first and second mechanisms—for example a piston, 116 and 120. In essence, first mechanism 116 imposes a force $F_1$, for pressing tissue 118 against frame 110 of device 100, at proximal end 108, while second mechanism 120 imposes a force $F_2$, which is substantially opposite in direction to $F_1$, for pressing sensor 122 against tissue 118. In other words, tissue 118 is pressed against sensor 122 and sensor 122 is pressed against tissue 118.

Each mechanism provides opposition to the other. The force $F_1$ ensures that tissue 118 will not move away from sensor 122, under the force $F_2$, and the force $F_1$ ensures that sensor 122 will not move away from tissue 118, under the force $F_1$. Operating together, first and second mechanisms— for example a piston 116 and 120 ensure that effective sensor-to-tissue contact is formed, at interface 45.

Alternatively, first mechanism 116 imposes a force $F_1$, a component of which presses tissue 118 against frame 110 of device 100, at proximal end 108, while second mechanism— for example a piston—120 imposes a force $F_2$, a component of which presses sensor 122 against tissue 118, so that components of each mechanism provide opposition to the other.

Thus, either the forces $F_1$ and $F_2$, or components thereof, ensure that tissue 118 will not move away from sensor 122 and that sensor 122 will not move away from tissue 118, so that effective sensor-to-tissue contact is formed, at interface 45.

Reference is now made to FIG. 1H, which schematically illustrates effective sensor-to-tissue contact, as a consequence of the balance of force diagram of FIG. 1G, in accordance with the present embodiments.

As seen in FIG. 1H, the interface 45 is substantially free of bubbles 46, foreign inclusions 47, and tissue folds 48, leading to effective contact, between the tissue 118 and the sensor 122, the effective contact being defined as a contact level of at least 95%, preferably, at least 98%, and more preferably, at least 99.8%.

Additionally, in accordance with embodiments of the present invention, which relate to sensors, operating with a wavelength λ, the effective contact may be further defined as a contact, for which the relationship between the wavelength λ and an average distance t1, the average distance after achieving effective contact, (see FIG. 1H) is such that t1<λ/3, and preferably, t1<λ/10, and more preferably, t1<λ/100.

Additionally or alternatively, the effective contact may be defined in absolute terms. Accordingly, the average distance t1 is less than 500 Angstroms, preferably the average distance t1 is less than 50 Angstroms, and more preferably, the average distance t1 is less than 5 Angstroms.

Reference is now made to FIGS. 2A-2C, which schematically illustrate the operation of proximal portion 106 of the device 100.

As seen in FIG. 2A, illustrating a first step, device 121, which is preferably a hand-held device, is physically brought proximally to tissue 118, for example, by hand.

As seen in FIG. 2B, illustrating a second step, tissue 118 is attached to device 121, via first mechanism 116, for example, by suction, along orifices 140.

As seen in FIG. 2C, illustrating a third step, second mechanism 120 is deployed, for pressing sensor 122 against tissue surface 119, forming substantially the single interface 45.

At this point, effective sensor-to-tissue contact has been formed, substantially, as described in FIG. 1F, and tissue characterization may take place, by the sensor 122.

Reference is now made to FIGS. 3A-3C, illustrating side and top cross sectional views of first mechanism 116 for attaching device 100 to tissue surface 119 according to the preferred embodiment of the present invention.

Frame 110 at proximal end 108 is preferably shaped as two concentric circles, of an inner diameter 112 and an outer diameter 114. Furthermore, inner diameter 112 is configured to allow piston 120 to advance therethrough towards tissue surface 119 so that proximal end 126 of piston 120 protrudes beyond frame 110, so as to press against tissue 118 which is attached to frame 110.

Additionally, frame 110 is provided with at least two orifices 140, preferably arranged between circumferences 112 and 114. Additionally, more orifices, for example, eight orifices may be used, as shown in FIG. 3B. Furthermore, suction is employed through the orifices 140 for attaching tissue surface 119 of tissue 118 to frame 110 (FIG. 1A). Moreover the suction is employed via duct system 142.

In FIG. 3C a flexible skirt 144 is added to outer diameter 114 of frame 110 for providing improved suction when attaching tissue 118 to proximal portion 106. Preferably, flexible skirt 144 is made of a resilient material, for example, natural or synthetic rubber.

Reference is now made to FIGS. 4A-4D, illustrating side and top cross sectional views of the first mechanism 116 for attaching the device to the tissue surface according to another embodiment of the present invention using a gripping device 150.

According to the embodiment described in FIGS. 4A-D, gripping device 150 is positioned on frame 110. Additionally, gripping device 150 comprises an at least two claws 152 configured to be in either a released state (as shown in FIG. 4C) or a gripping state (as shown in FIG. 4D). Preferably, at least two claws 152 are arranged on frame 110 (eight claws are shown in FIG. 4B). Prior to gripping tissue 118, proximal portion 106 is positioned close to tissue surface 119 with at least two claws 152 being in a retracted position. The claws are then brought to a gripping state, thus attaching tissue 118 to proximal portion 106 and completing the first stage of creating effective sensor-to-tissue contact between sensor 122 of device 100 and tissue surface 119.

Figure 5B:
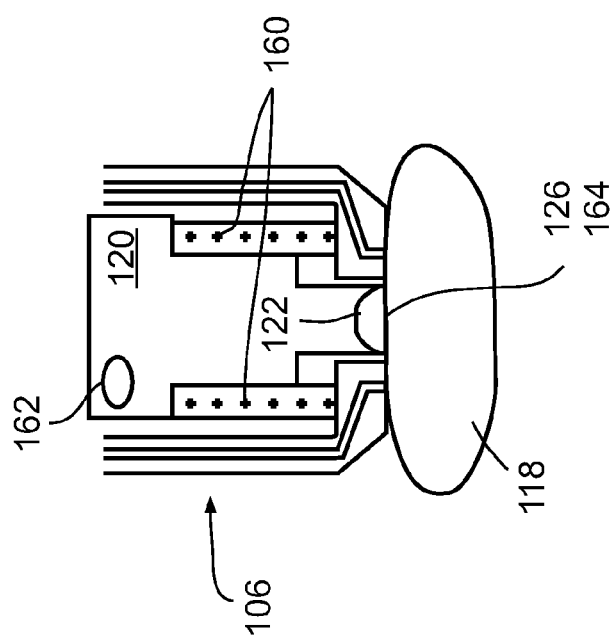

Reference is now made to FIGS. 5A-5B schematically illustrating a side cross sectional view of the second mechanism 120, for forming effective sensor-to-tissue contact, according to one embodiment of the present invention.

Second mechanism 120 is preferably a piston 120 having a tissue characterizing sensor 122 at proximal end 126. Piston 120 is configured to slide smoothly from a retracted position (shown in FIG. 5A) to a deployed position (shown in FIG. 5B) in which effective contact between tissue 118 and tissue characterizing sensor 122 is established. Advancing piston 120 towards tissue 118 may be controlled by at least one spring 160. Furthermore, advancing piston 120 towards tissue 118 may be actuated using a switch 162. Preferably, a surface 164 of proximal end 126 of piston 120 is highly polished, for creating the effective contact with tissue 118.

Figure 6:
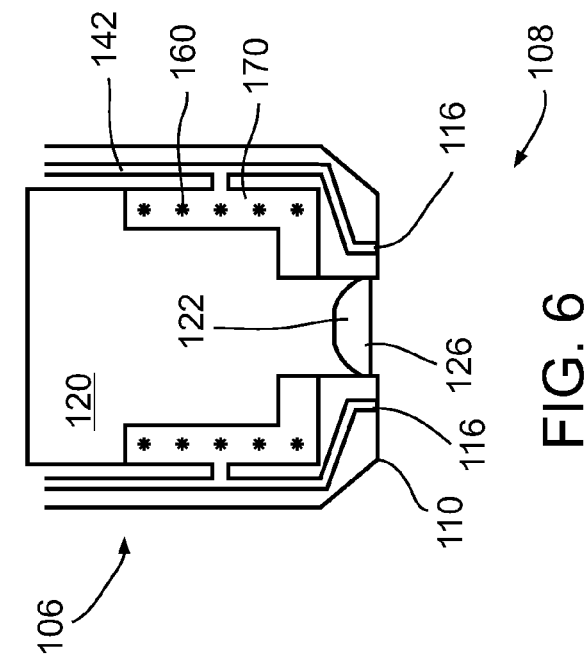
FIG. 6 schematically illustrates a side cross-sectional view of the proximal end of the device for tissue characterization, showing a second mechanism, for forming effective sensor-to-tissue contact, according to another embodiment of the present invention.

Reference is now made to FIG. 6, schematically illustrating a side cross sectional view of proximal portion 106 of device 100 for tissue characterization, according to another embodiment of the present invention.

According to the present embodiment, spring 160 is contained within a spring tunnel 170, which is connected to duct system 142. Therefore, piston 120 is actuated by the suction created in spring tunnel 170, responsive to the partial pressure in duct system 142, when orifices 140 are closed, as first mechanism 116 attaches tissue 118 to device 100 at proximal end 108.

Figure 7:
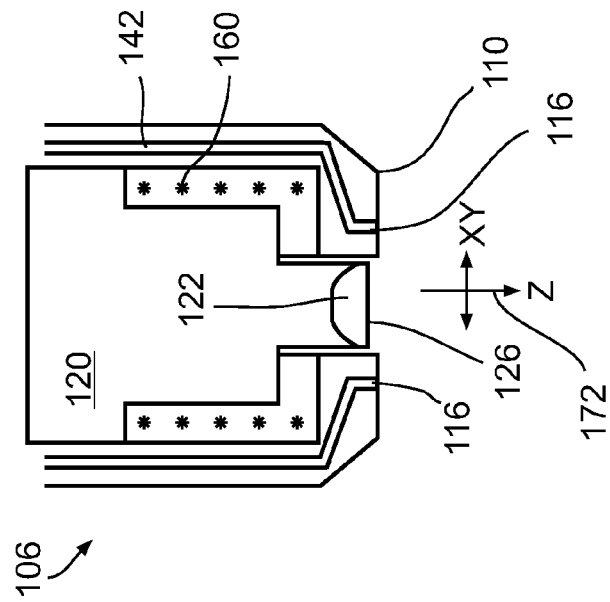
FIG. 7 schematically illustrates a side cross-sectional view of the proximal end of the device for tissue characterization showing the second mechanism, for forming effective sensor-to-tissue contact, according to yet another embodiment of the present invention.

Reference is now made to FIG. 7, schematically illustrating a side cross sectional view of proximal portion 106 of device 100 for tissue characterization, according to yet another embodiment of the present invention.

The present embodiment also illustrates a coordinate system 172. Piston 120 slides towards tissue 118 along a Z axis, perpendicular to frame 110, while vibrating in an XY-plane, perpendicular to Z axis. The vibration motion in XY-plane allows for a gliding motion against tissue 118, which in effect removes, as if by sweeping, any foreign matter, or entrapped gases or liquids, from the interface 45 (FIG. 2C).

Reference is now made to FIGS. 8A-8D, which schematically illustrate manners of controlling the travel of piston 120, according to two alternative embodiments of the present invention FIGS. 8A and 8B schematically illustrate piston 120 in retracted and deployed positions, respectively, according to a first embodiment. Piston 120 has a fixed travel d, shown as 180, wherein the construction of proximal portion 106 operates as a stop, to ensure the fixed travel. Alternatively, the fixed travel is reached when spring 160 is compressed to its maximum value. Preferably, distance d is between about 1 mm and about 50 mm.

FIGS. 8C and 8D schematically illustrate piston 120 in retracted and deployed positions, respectively, according to a second embodiment. The advancement of piston 120 and of sensor 122 is such that a force F3, exerted on piston 120, in the −z direction is exactly balanced by the force, which the attached tissue 118 imposes on sensor 122, in the +z direction, and by the force contracted spring 160 imposes on piston 120 in the +z direction.

Reference is now made to FIGS. 9A-9D, which schematically illustrate various geometries for the proximal ends 126 of the sensor 122, in accordance with embodiments of the present invention.

Figure 9D:
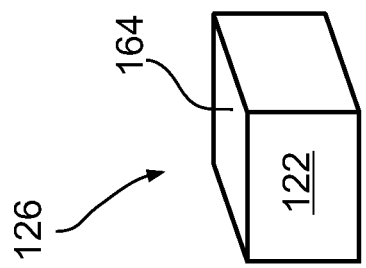
FIGS. 9A-9D schematically illustrate various geometries for the proximal ends of the sensor, in accordance with the present invention.
Figure 9C:
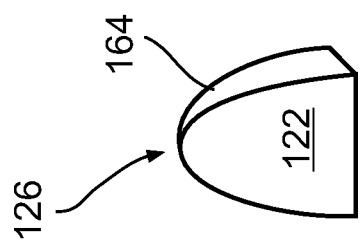
Figure 9B:
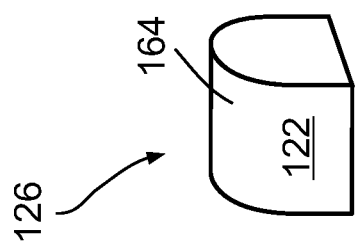
Figure 9A:
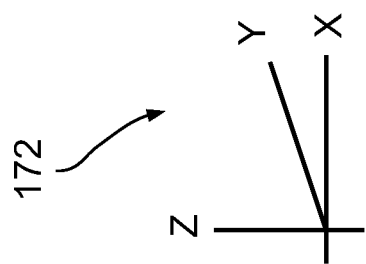

FIG. 9A provides the reference coordinate system 172.

FIG. 9B schematically illustrates a roller-shaped sensor 122, and its polished surface 164, at proximal end 126.

FIG. 9C schematically illustrates a dome-shaped sensor 122, and its polished surface 164, at proximal end 126.

FIG. 9D schematically illustrates a cube-shaped sensor 122, and its polished surface 164, at proximal end 126.

It will be appreciated that other shapes are also possible.

Reference is now made to FIGS. 10A-10D, schematically illustrating a prototype of device 100, for tissue characterization, in accordance with a preferred embodiment of the present invention. Prototype device 100 illustrated here is generally applied when perpendicular to tissue 118, so that its length axis L is along the Z axis, while tissue surface 119 (FIGS. 2A-2C) is generally in the X-Y plane. Device 100 preferably has a length of between about 50 mm and about 300 mm, and a diameter of between about 10 mm and about 150 mm. It will be appreciated that other dimensions are similarly possible. Structure 101 of device 100 is preferably made of a rigid material, for example, a rigid plastic, ceramics, wood, or the like. Vacuum outlet 105 is adapted for connecting to a pump.

Reference is now made to FIGS. 11A-11D, schematically illustrating another prototype of the device 100, for tissue characterization, in accordance with yet another preferred embodiment of the present invention. Prototype device 100 illustrated here is shaped as an arm 300 having housing 103 at a proximal end 302 of arm 300. Prototype device 100 illustrated in FIGS. 11A-11D is generally applied when parallel to tissue 118, so that its length axis L and the tissue surface 119 are both in the X-Y plane and sensor 122 moves in the Z plane. Preferably, flexible skirt 144 is provided at proximal end of housing 103 for assisting in attaching tissue 118 to frame 110.

Figure 12:
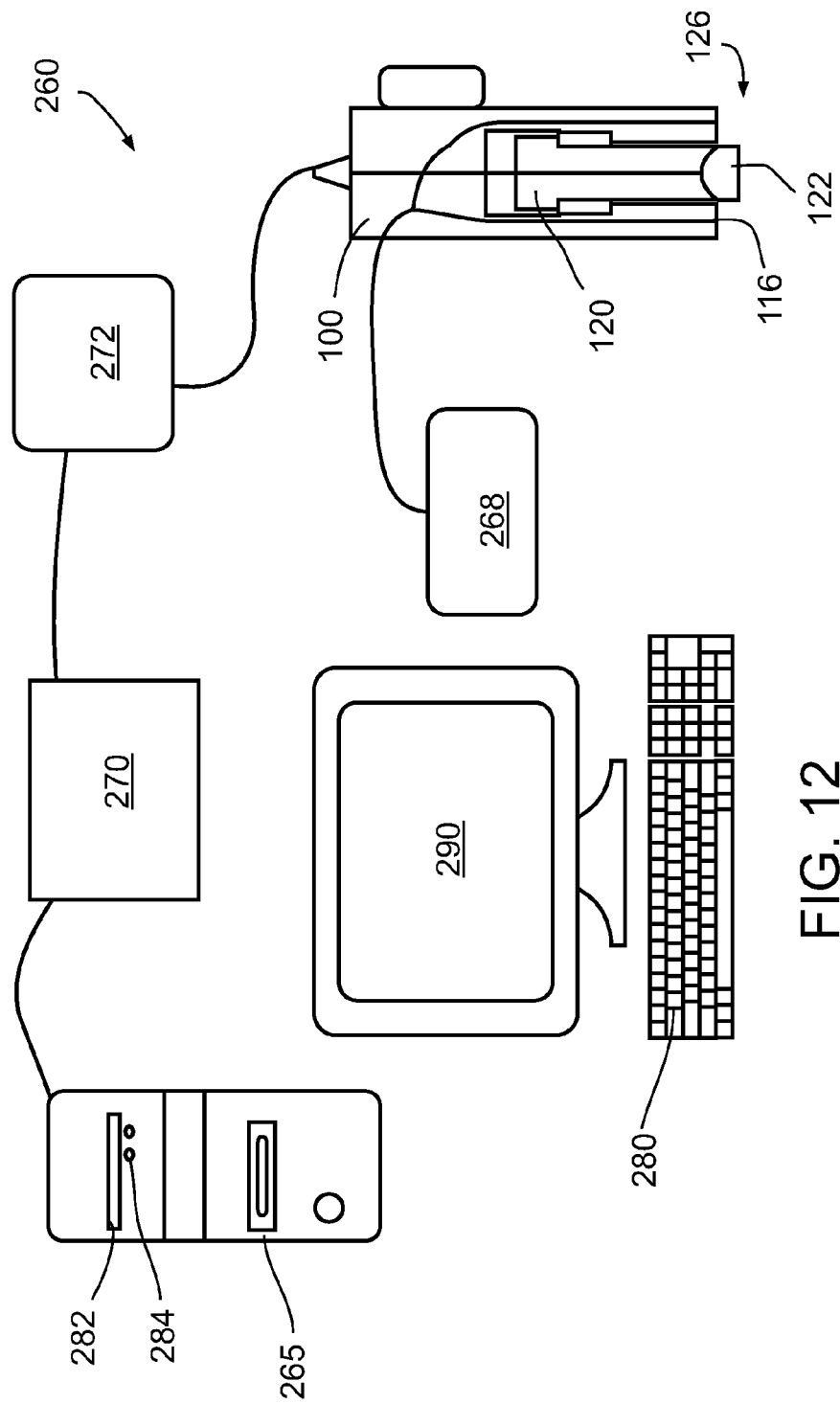
FIG. 12 schematically illustrates an overall system for tissue characterization, in accordance with the present invention.

Reference is now made to FIG. 12, schematically illustrating an overall system for tissue characterization, in accordance with an embodiment of the present invention.

System 260 includes device 100, having sensor 122.

A signal generator 272 provides sensor 122 with a signal and a signal analyzer 270 receives and analyzes signals from sensor 122. It will be appreciated that signal generator 272 and signal analyzer 270 may be integrated into a single unit.

For example, where the sensor 122 is a dielectric-property sensor, constructed essentially as coaxial cable, units 270 and 272 may include, for example, an impedance analyzing external unit, such as Agilent 4396A, and a test fixture connected via a coaxial cable to the impedance analyzing external unit. The sensors may be battery operated or associated with power supply units.

It will be appreciated that units 270 and 272 will complement the specific sensor 122. For example, where sensor 122 is an optical sensor, unit 272 may be a light emitting diode or a laser, and unit 270 may be an optical analyzer or a charge coupled device (CCD).

A computer 265, which may be a personal computer, a laptop, a palmtop, a microcomputer, or another computer, as known, may also be used for additional data analysis. Preferably, computer 265 includes a user interface, for example, a keyboard 280, or knobs, and may further include storage systems, such as a read and write drive 282, a USB port 284, and a display screen 290.

Reference is now made to FIGS. 13A-13E, schematically illustrating cross sectional side views of piston 120 containing sensor 122. The illustrations show a variety of sensors for characterizing the tissue after the tissue surface is brought to effective contact with the sensor, according to preferred embodiments of the present invention.

Sensor 122 may be a dielectric-property sensor, an optical sensor, an MRI sensor, an RF sensor, a MW sensor, an X-ray sensor, an ultrasound sensor, a biosensor, a chemical sensor, a mechanical sensor, a temperature sensor, an infrared thermography sensor, or another sensor, as known.

Figure 13A:
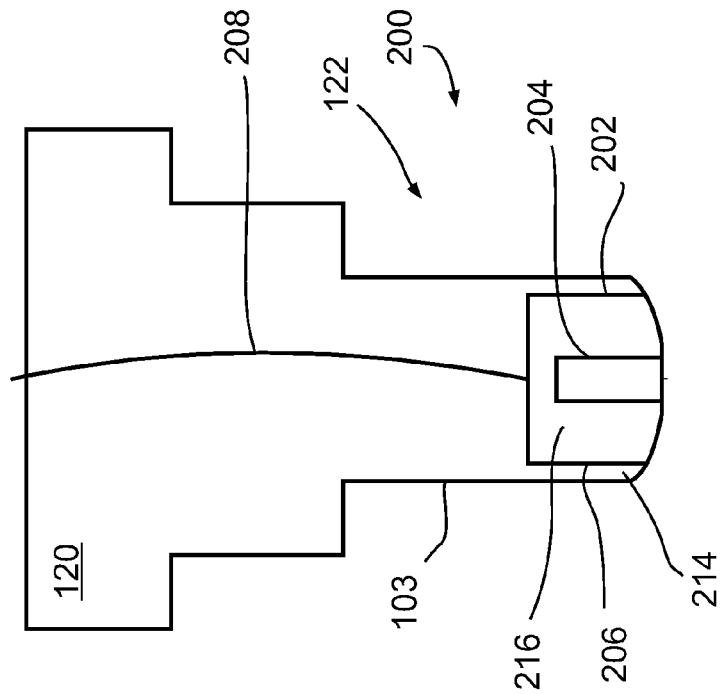
Figure 13B:
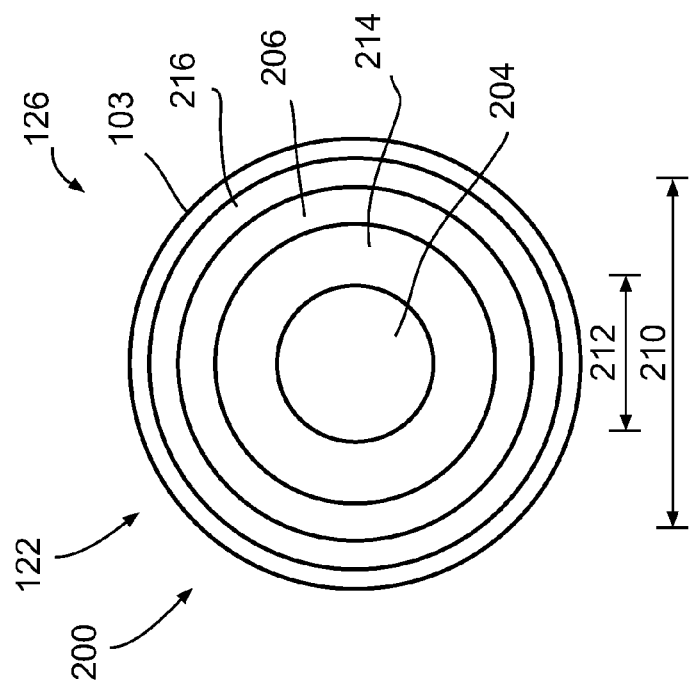

FIGS. 13A and 13B illustrate a side cross-sectional view and a view from proximal end 126, respectively, of piston 120 and sensor 122. According to the present embodiment, sensor 122 is a dielectric-property sensor 200, for measuring the dielectric properties of tissue 118, for example, as taught by commonly owned U.S. Pat. No. 6,813,515 and commonly owned PCT publication WO 03/060462, both of whose disclosures are incorporated herein by reference. By comparing the results with known tissue dielectric properties, or by evaluating generated pulses with those reflected from the tissue, the characteristics of tissue 118 can be determined. Furthermore, dielectric-property sensor 200 may be constructed as a coaxial cable 202, having an inner electrode 204 and an outer electrode 206, separated by a layer of insulation. Outer electrode 206 may be grounded. Preferably, coaxial cable 202 is located within piston 120. Signals from dielectric-property sensor 200 are transferred for analysis through a transmission line 208 to a computerized system 260, described hereinbelow in conjunction with FIG. 12.

Preferably, inner electrode 204 has a diameter 212 of between about 0.2 and 1.5 mm, and outer electrode 206 has an inner diameter 210 of between about 3.0 and 10.0 mm, and is about 0.5 mm thick. It will be appreciated that other dimensions, which may be larger or smaller, may similarly be used.

Additionally, outer electrode 206 may be covered with an insulating sheath 214 made of an insulating material, for example, Teflon. The dielectric-property sensor 200 may be encased in a filler material 216, for example epoxy, which may be formed as a plug that fits into piston 120.

FIG. 13C illustrates piston 120 comprising sensor 122 formed as an RF or MW horn antenna 230 mounted on piston 120, in accordance with still another embodiment of the present invention. RF or MW horn antenna 230 is associated with an RF/MW transmission line or wave guide 232, while units 270 and 272 (FIG. 12) are RF/MW generation, collection and analysis units. The present embodiment relies on RF microwave characterization by the generation of propagating radiation in the RF microwave region of the electromagnetic spectrum, towards the tissue, and measuring its reflection. The radiation is usually transmitted and received by an antenna, for example the horn antenna 230. The tissue characterization is done by analyzing the amplitude and phase difference between the original waves and the reflected wave.

FIG. 13D illustrates piston 120 comprising sensor 122 formed as an optical sensor 240 mounted on piston 120, in accordance with yet another embodiment of the present invention. An optical signal is generated in an external unit, such as unit 270 (FIG. 12) and transmitted via an optical fiber 242 to tissue 118. The reflection of the light is then received in a dedicated module inside the optical unit. The optical energy is usually transmitted to and from tissue 118 via a lens 244.

The details of optical signal generation, receiving and analyzing depend on the specific optical method that is chosen. For example, for reflection spectroscopy, tissue characterization relies on measuring the relative amplitude and phase of the reflected light versus the generated light. An example for the reflection spectroscopy method is described in commonly owned U.S. patent application Ser. No. 10/298,196, whose disclosure is incorporated herein by reference. It will be appreciated that other methods may be used, as known.

Alternatively, auto florescence may be used, for measuring emitted radiation, from the tissue, at a wavelength different than that originally transmitted. The emitted radiation occurs in response to excitation by impinging radiation, and may be used for tissue characterization, for example, as used by Xillix Technologies Corp. It will be appreciated that other methods may be used, as known.

FIG. 13E illustrates piston 120 comprising sensor 122 being an MRI sensor 250 mounted on piston 120, in accordance with yet another embodiment of the present invention. MRI sensor 250 has a permanent magnet 252, enclosed in an RF coil 254, for example, as taught in commonly owned US Patent Application Publication No. 2005/0021019 to Hashimshony et al., entitled "Method and apparatus for examining substance, particularly tissue, to characterize its type," whose disclosure is incorporated herein by reference, and in U.S. Pat. No. 5,572,132, to Pulyer, et al., entitled, "MRI probe for external imaging," whose disclosure is incorporated herein by reference.

In accordance with the present embodiments, tissue characterization may be performed by various techniques, including any one of the following nonexhaustive list, or by another technique.

Tissue Characterization by Ultrasonography:

Ultrasonography is a medical imaging technique, using high frequency sound waves in the range of about 1 to 20 MHz and their echoes. The sound waves travel in the body and are reflected by interfaces between different types of tissues, such as between a healthy tissue and a denser cancerous tissue, or between a portion of a soft tissue and a bone. The ultrasound probe receives the reflected sound waves and the associated instrumentation calculates the distances from the probe to the reflecting boundaries.

The ultrasound probe includes a piezoelectric crystal, which produces an electric signal in response to a pressure pulse. The shape of the probe determines its field of view, and the frequency of the emitted sound determines the minimal detectable object size. Generally, the probes are designed to move across the surface of the body. However, some probes are designed to be inserted through body lumens, such as the vagina or the rectum, so as to get closer to the organ being examined.

Before the early 1970's ultrasound imaging systems were able to record only the strong echoes arising from the outlines of an organ, but not the low-level echoes of the internal structure. In 1972 a refined imaging mode was introduced called gray-scale display, in which the internal texture of many organs became visible. In consequence, ultrasound imaging became a useful tool for imaging tumors, for example, in the liver.

A development of recent years is 3D ultrasound imaging, in which; several two-dimensional images are acquired by moving the probes across the body surface or by rotating probes; inserted into body lumens. The two-dimensional scans are then combined by specialized computer software to form 3D images.

In multiple-element probes, each element has a dedicated electric circuit, so that the beam can be "steered" by changing the timing in which each element sends out a pulse. By sequentially stimulating each element, the beams can be rapidly steered from the left to right, to produce a two-dimensional cross sectional image. Additionally, transducer-pulse controls allow the operator to set and change the frequency and duration of the ultrasound pulses, as well as the scan mode of the machine. A probe formed of array transducers has the ability to be steered as well as focused.

Contrast agents may be used in conjunction with ultrasound imaging, for example as taught by U.S. Pat. No. 6,280,704, to Schutt, et al., entitled, "Ultrasonic imaging system utilizing a long-persistence contrast agent," whose disclosure is incorporated herein by reference.

Tissue Characterization by its Dielectric Properties:

There are several known techniques for local tissue characterization by the tissue's electromagnetic properties.

Commonly owned U.S. Pat. No. 6,813,515, to Hashimshony, entitled, "Method and system for examining tissue according to the dielectric properties thereof," whose disclosure is incorporated herein by reference, describes a method and system for examining tissue in order to differentiate it from other tissue, according to the dielectric properties of the examined tissue. The method includes applying an electrical pulse to the tissue to be examined via a probe formed with an open cavity such that the probe generates an electrical fringe field in examined tissue within the cavity and produces a reflected electrical pulse therefrom with negligible radiation penetrating into other tissues or biological bodies near the examined tissue; detecting the reflected electrical pulse; and comparing electrical characteristics of the reflected electrical pulse with respect to the applied electrical pulse to provide an indication of the dielectric properties of the examined tissue.

Furthermore, commonly owned U.S. Provisional Application No. 60/641,081, entitled, "Device and Method for Tissue Characterization in a Body Lumen, by an Endoscopic Electromagnetic Probe," whose disclosure is incorporated herein by reference, discloses a device and method for tissue characterization in a body lumen, for the detection of abnormalities, using an electromagnetic probe, mounted on an endoscope. The endoscope may be designed for insertion in a body lumen, selected from the group consisting of an oral cavity, a gastrointestinal tract, a rectum, a colon, bronchi, a vagina, a cervix, a urinary tract, and blood vessels. Additionally, it may be designed for insertion in a trucar valve.

Additionally, commonly owned U.S. Provisional Application No. 60/665,842, entitled, "Electromagnetic Sensors for tissue Characterization," whose disclosure is incorporated herein by reference, discloses a sensor, comprising: a resonating element, formed as a conductive structure, configured to be placed proximally to an edge of a tissue for characterization, without penetrating the tissue, and having a diameter-equivalent D, which defines a cross-sectional area of the resonating element, on a plane substantially parallel with the edge; and at least one conductive lead, for providing communication with an external system, wherein the resonating element is configured to resonate at a free-air wavelength range of between about $\lambda$ and about $10\lambda$, wherein $\lambda$ is at least about ten times the diameter-equivalent D, and wherein upon receiving a signal in the range of between about $\lambda$ and about $10\lambda$, the sensor is configured to induce electric and magnetic fields, in a near zone, in the tissue, the near zone being a hemisphere having a diameter of substantially D, beginning with the edge, while causing negligible radiation in a far zone, so that the tissue, in the near zone, effectively functions as part of the resonating element, varying a resonating response to the sensor, and so the tissue, in the near zone, is thereby characterized by its electromagnetic properties, by the resonating response to the sensor.

Tissue Characterization by Electrical Impedance Imaging:

Electrical impedance imaging relates to measuring the impedance between a point on the surface of the skin and some reference point on the body of a patient. Sometimes, a multi-element probe, formed as a sheet having an array of electrical contacts, is used for obtaining a two-dimensional impedance map of the tissue, for example, the breast. The two-dimensional impedance map may be used, possibly in conjunction with other data, such as mammography, for the detection of cancer.

Rajshekhar, V. ("Continuous impedance monitoring during CT-guided stereotactic surgery: relative value in cystic and solid lesions," Rajshekhar, V., British Journal of Neurosurgery, 1992, 6, 439-444) describes using an impedance probe with a single electrode to measure the impedance characteristics of lesions. The objective of the study was to use the measurements made in the lesions to determine the extent of the lesions and to localize the lesions more accurately. The probe was guided to the tumor by CT and four measurements were made within the lesion as the probe passed through the lesion. A biopsy of the lesion was performed using the outer sheath of the probe as a guide to position, after the probe itself was withdrawn.

U.S. Pat. No. 4,458,694, to Sollish, et al., entitled, "Apparatus and method for detection of tumors in tissue," whose disclosure is incorporated herein by reference, relates to an apparatus for detecting tumors in human breast, based on the dielectric constants of localized regions of the breast tissue. The apparatus includes a probe, including a plurality of elements. The apparatus further includes means for applying an AC signal to the tissue, means for sensing dielectric properties at each of the probe elements at different times, and signal processing circuitry, coupled to the sensing means, for comparing the dielectric properties sensed at the different times. The apparatus thus provides an output of the dielectric constants of localized regions of breast tissue associated with the probe.

Similarly, U.S. Pat. No. 4,291,708 to Frei, et al., entitled, "Apparatus and method for detection of tumors in tissue," whose disclosure is incorporated herein by reference, relates to apparatus for detecting tumors in human breast tissue, by the dielectric constants of a plurality of localized regions of human breast tissue.

U.S. Pat. Nos. 6,308,097, 6,055,452 and 5,810,742, to Pearlman, A. L., entitled, "Tissue characterization based on impedance images and on impedance measurements," whose disclosures are incorporated herein by reference, describe apparatus for aiding in the identification of tissue type for an anomalous tissue in an impedance image. The device comprises: means for providing a polychromic emmitance map of a portion of the body; means for determining a plurality of polychromic measures from one or both of a portion of the body; and a display of an indication based on said plurality of polychromic measures.

Tissue Characterization by Optical Fluorescence Spectroscopy:

When a sample of large molecules is irradiated, for example, by laser light, it will absorb radiation, and various levels will be excited. Some of the excited states will return back substantially to the previous state, by elastic scattering, and some energy will be lost in internal conversion, collisions and other loss mechanisms. However, some excited states will create fluorescent radiation, which, due to the distribution of states, will give a characteristic wavelength distribution.

Some tumor-marking agents give well-structured fluorescence spectra, when irradiated by laser light. In particular, hematoporphyrin derivatives (HPD), give a well-structured fluorescence spectrum, when excited in the Soret band around 405 nm. The fluorescence spectrum shows typical peaks at about 630 and 690 nm, superimposed in practice on more unstructured tissue autofluorescence. Other useful tumor-marking agents are dihematoporphyrin ether/ester (DHE), hematoporphyrin (HP), polyhematoporphyrin ester (PHE), and tetrasulfonated phthalocyanine (TSPC), when irradiated at 337 nm ($N_2$ laser).

U.S. Pat. No. 5,115,137, to Andersson-Engels, et al, entitled, "Diagnosis by means of fluorescent light emission from tissue," whose disclosure is incorporated herein by reference, relates to improved detection of properties of tissue by means of induced fluorescence of large molecules. The tissue character may then be evaluated from the observed large-molecule spectra. According to U.S. Pat. No. 5,115,137, the spectrum for tonsil cancer is clearly different from normal mucosa, due to endogenous porphyrins.

U.S. Pat. No. 6,258,576, to Richards-Kortum, et al., entitled, "Diagnostic method and apparatus for cervical squamous intraepithelial lesions in vitro and in vivo using fluorescence spectroscopy," whose disclosure is incorporated herein by reference, relates to the use of multiple illumination wavelengths in fluorescence spectroscopy for the diagnosis of cancer and precancer, for example, in the cervix. In this manner, it has been possible to (i) differentiate normal or inflamed tissue from squamous intraepithelial lesions (SILs) and (ii) differentiate high grade SILs from non-high grade SILs. The detection may be performed in vitro or in vivo. Multivariate statistical analysis has been employed to reduce the number of fluorescence excitation-emission wavelength pairs needed to re-develop algorithms that demonstrate a minimum decrease in classification accuracy. For example, the method of the aforementioned patent may comprise illuminating a tissue sample with electromagnetic radiation wavelengths of about 337 nm, 380 nm and 460 μm, to produce fluorescence; detecting a plurality of discrete emission wavelengths from the fluorescence; and calculating from the emission wavelengths a probability that the tissue sample belongs in particular tissue classification.

Commonly owned U.S. Patent Application Publication No. 2003/01383786, to Hashimshony, entitled, "Method and apparatus for examining tissue for predefined target cells, particularly cancerous cells, and a probe useful for such method and apparatus," whose disclosure is incorporated herein by reference, teaches a method apparatus and probe for examining tissue and characterizing its type according to measured changes in optical characteristics of the examined tissue. In a preferred embodiment of this method the tissue to be examined is subject to a contrast agent containing small particles of a physical element conjugated with a biological carrier selectively bindable to the target cells. Additionally, energy pulses are applied to the examined tissue, and the changes in impedance and/or the optical characteristics produced by the applied energy pulses are detected and utilized for determining the presence of the target cells in the examined tissue. Furthermore, in a preferred embodiment, the applied energy pulses include laser pulses, and the physical element conjugated with a biological carrier is a light-sensitive semiconductor having an impedance which substantially decrease in the presence of light. Moreover, the same probe used for detecting the targeted cells, may also be used for destroying the cells so targeted.

Tissue Characterization by Optical Reflectance Spectroscopy:

The application optical reflectance spectroscopy for tissue characterization is described, for example, at the world wide web location sbsp-limb.nichd.nih.gov/html/spectroscopy.html, downloaded on Mar. 15, 2005, disclosing an optical reflectance spectroscopy (ORS) device for measuring the thickness of the epithelial layer, and an evaluation technique based on oblique angle reflectance spectroscopy, that allows assessment of the scattering and absorption properties of the epithelium and stroma, thus providing information on chronic oral epithelial tissue inflammation, which is considered a potential diagnostic precursor to oral cancer.

Additionally, Tomatis, A., et al, studied reflectance images of 43 pigmented lesions of the skin (18 melanomas, 17 common melanocytic naevi and eight dysplastic naevi). Reflectance images were acquired by a telespectrophotometric system and were analyzed in the spectral range from 420 to 1040 nm, to discriminate melanoma from benign melanocytic entities. Different evaluations were carried out considering the whole spectrum, the visible and the near infrared. A total of 33 (76.7%) lesions were correctly diagnosed by the telespectrophotometric system, compared with 35 (81.4%) correct clinical diagnoses. Reflectance in the infrared band appears diagnostically relevant.

Tissue Characterization by Magnetic Resonance Imaging (MRI):

Magnetic resonance imaging is based on the absorption and emission of energy in the radio frequency range of the electromagnetic spectrum, by nuclei having unpaired spins.

Conventional MRI is a large-apparatus, for whole body imaging, having:

i. a primary magnet, which produces the $B_o$ field for the imaging procedure;
ii. gradient coils for producing a gradient in $B_o$;
iii. an RF coil, for producing the $B_1$ magnetic field, necessary to rotate the spins by 90° or 180° and for detecting the MRI signal; and
iv. a computer, for controlling the components of the MRI imager.

Generally, the magnet is a large horizontal bore superconducting magnet, which provides a homogeneous magnetic field in an internal region within the magnet. A patient or object to be imaged is usually positioned in the homogeneous field region located in the central air gap for imaging. A typical gradient coil system comprises an anti-Helmholtz type of coil. These are two parallel ring shaped coils, around the z axis. Current in each of the two coils flows in opposite directions creating a magnetic field gradient between the two coils.

The RF coil creates a B1 field, which rotates the net magnetization in a pulse sequence. The RF coils may be: 1) transmit and receive coils, 2) receive only coils, and 3) transmit only coils.

As described hereinabove, the MRI relies on a magnetic field in an internal region within the magnet. As such, it is unsuitable as a handheld probe or an endoscopic probe, because the tissue to be imaged has to be in the internal region of the imager, However, U.S. Pat. No. 5,572,132, to Pulyer, et al., entitled, "MRI probe for external imaging," whose disclosure is incorporated herein by reference, describes an MRI spectroscopic probe having an external background magnetic field B0 (as opposed to the internal background magnetic filed of the large horizontal bore superconducting magnet.). Thus, an MRI catheter for endoscopical imaging of tissue of the artery wall, rectum, urinal tract, intestine, esophagus, nasal passages, vagina and other biomedical applications may be constructed. The probe comprises (i) a miniature primary magnet having a longitudinal axis and an external surface extending in the axial direction, and (ii) a RF coil surrounding and proximal to said surface. The primary magnet is structured and configured to provide a symmetrical, preferably cylindrically shaped, homogeneous field region external to the surface of the magnet. The RF coil receives NMR signals from excited nuclei. For imaging, one or more gradient coils are provided to spatially encode the nuclear spins of nuclei excited by an RF coil, which may be the same coil used for receiving NMR signals or another RF coil.

Additionally, commonly owned US Patent Application Publication No. 2005/0021019 to Hashimshony et al., entitled "Method and apparatus for examining substance, particularly tissue, to characterize its type," whose disclosure is incorporated herein by reference, describes a method and apparatus for examining a substance volume to characterize its type, by: applying a polarizing magnetic field through the examined substance: applying RF pulses locally to the examined substance volume such as to invoke electrical impedance (EI) responses signals corresponding to the electrical impedance of the substance, and magnetic resonance (MR) responses signals corresponding to the MR properties of the substance; detecting the EI and MR response signals; and utilizing the detected response signals for characterizing the examined substance volume type.

Contrast agents may be used in conjunction with MRI. For example, U.S. Pat. No. 6,315,981 to Unger, entitled, "Gas filled microspheres as magnetic resonance imaging contrast agents," whose disclosure is incorporated herein by reference, describes the use of gas filled microspheres as contrast agents for MRI.

Additionally, U.S. Pat. No. 6,747,454, to Belt, entitled, "Array of coils for use in imaging the vasculature of a patient," whose disclosure is incorporated herein by reference, describes an array of coils, configured for use in imaging the vasculature of a patient.

Furthermore, U.S. Pat. No. 6,677,755, to Belt, et al., "Circuit for selectively enabling and disabling coils of a multi-coil array," whose disclosure is incorporated herein by reference, describes a circuit, used to selectively enable and disable n-coils. The circuit includes n-drivers powered by a current source. Each n-driver includes a pair of FETs disposed such that a gate of one FET is connected to a gate of the other FET to form a common gate node thereat. The n-drivers are disposed in a totem-pole configuration. The one FET of a first of the n-drivers has (A) a drain linked to a ground and to an end of a first of the n-coils and (B) a source linked to a drain of the one FET of a second of the n-drivers and to an end of a second of the n-coils. The other FET of the first of the n-drivers has (A) a source linked to an opposite end of the first of the n-coils and (B) a drain linked to the end of the second of the n-coils and to the source of the one FET of the first of the n-drivers. The one FET of the second of the n-drivers also has a source linked to a drain of the one FET of a next of the n-drivers and to an end of a next of the n-coils. The other FET of the second of the n-drivers also has (A) a source linked to an opposite end of the second of the n-coils and (B) a drain linked to the end of the next of the n-coils and to the source of the one FET of the second of the n-drivers. This continues until the one FET and the other FET of an nth of the n-drivers are likewise disposed in the totem-pole configuration of the n-drivers, with a source and a drain of the one FET and the other FET, respectively, of the nth of the n-drivers being connected to the current source. Each of the n-drivers is used to operate a corresponding one of the n-coils by being responsive at its common gate node (i) a coil disable signal by activating the one FET thereof and deactivating the other FET thereof thereby not only drawing current away from and thus disabling the corresponding coil but also allowing the current to flow through the one FET and thus be available as a source of current to a successive one of the n-drivers and (ii) a coil enable signal by deactivating the one FET thereof and activating the other FET thereof thereby allowing the current not only to flow serially through the corresponding coil and the other FET thus enabling the corresponding coil but also to be available as a source of current to the successive one of the n-drivers.

Tissue Characterization by Temperature Imaging:

Temperature Imaging for locating and detecting neoplastic tissue has been known, since the 1950's, when it was discovered that the surface temperature of skin in the area of a malignant tumor exhibited a higher temperature than that expected of healthy tissue. Thus, by measuring body skin temperatures, it became possible to screen for the existence of abnormal body activity such as cancerous tumor growth. With the development of liquid crystals and methods of forming temperature responsive chemical substrates, contact thermometry became a reality along with its use in medical applications. Devices employing contact thermometry could sense and display temperature changes through indicators, which changed colors, either permanently or temporarily, when placed in direct physical contact with a surface such as skin, reflecting a temperature at or near the point of contact. An abnormal reading would alert a user to the need for closer, more detailed examination of the region in question. However, the art in this area has been directed primarily at sensing and displaying temperatures on exterior skin surfaces.

U.S. Pat. No. 3,830,224, to Vanzetti et al., whose disclosure is incorporated herein by reference, disclosed the placement of temperature responsive, color changing liquid crystals at various points in a brassiere for the purpose of detecting the existence of breast cancer.

U.S. Pat. No. RE 32,000, to Sagi, entitled, "Device for Use in Early Detection of Breast Cancer," whose disclosure is incorporated herein by reference, disclosed a device comprising a flexible, heat-conductive web, preferably in the form of a disc-shaped patch having an adhesive layer on one side thereof and a peelable layer removably secured thereto by said adhesive layer. On the other side thereof, the device comprises an array of spaced-apart indicators, each of said indicators comprising a dye or a pigment and a temperature sensitive substance (crystalline organic chemical) which melts at a relatively precise temperature which is approximately 0.5.degree. F. different from the adjacent indicator. As many indicators are used as are necessary to cover the desired temperature range. The device is incorporated into the breast-receiving cups of a brassiere and mirror image quadrants of the two breasts are scanned and the device is visually examined to determine the number of indicators which have displayed a change in color, thus apprising the person of the existence of abnormality in the mammary tissue.

U.S. Pat. No. 6,135,968, to Brounstein, entitled, "Differential temperature measuring device and method", whose disclosure is incorporated herein by reference, describes a device and method for sensing temperatures at internal body locations non-surgically accessible only through body orifices. The device is particularly useful in medical applications such as screening for cancer and other abnormal biological activity signaled by an increase in temperature at a selected site. As applied to prostate examinations, the device is temporarily, adhesively affixed to a user's fingertip or to a mechanical probe. In the preferred embodiment, the device includes two temperature-sensing elements, which may include a plurality of chemical indicators. Each indicator changes color in response to detection of a predetermined particular temperature. When properly aligned and installed, the first element is located on the palmar surface of the fingertip while the second element is located on the dorsal surface of the fingertip. After an examination glove has been donned over the fingertip carrying the device, a prostate examination is performed during which the first element is brought into constant but brief contact with the prostate region and the second element is similarly, simultaneously brought into contact with a dermal surface opposing the prostate region. Upon withdrawal of the fingertip from the rectum and removal of the glove, the two temperature sensing elements may be visually examined in order to determine the temperatures detected by each one. A significant difference in observed temperatures indicates the possibility of abnormal biological activity and the need for further diagnostic or medical procedures.

Tissue Characterization using Biosensors:

Biosensors may be of catalytic type that integrated enzymes, cellular organelles, tissues or whole microorganisms with transducers that convert a biological response into a digital electronic signal. The principal transducers used are electrochemical, optical, or thermometric. Biosensors may also be of affinity type. Affinity biosensors deliver information about the binding of antibodies to antigens, cell receptors to their ligands, and DNA and RNA to nucleic acid with a complementary sequence. Still, additional types are fully integrated biochip devices that perform as micro bio-reactors. All types can be used in high-density arrays of bio-molecular sensors.

Some of these sensors are further discussed in:

(i) Enzyme and Microbial Biosensors: Techniques and Protocols. Ed. A. Mulchandani & K. R. Rogers (Humana Press, 1998);

(ii) Affinity Biosensors: Techniques and Protocols. Ed. A. Mulchandani & K. R. Rogers (Humana Press, 1998);

(iii) Journal: Biosensors & Bioelectronics:
 a. Volume 20, Issue 8, Pages 1459-1695 (15 Feb. 2005);
 b. Volume 20, Issue 6, Pages 1029-1259 (15 Dec. 2004);
 c. Volume 20, Issue 5, Pages 917-1028 (15 Nov. 2004);
 d. Volume 20, Issue 1, Pages 1-142 (30 Jul. 2004); and
 e. Volume 20, Issue 12, Pages 2387-2593 (15 Jun. 2005); and (iv) Journal: Sensors & actuators B (chemical). Volume:
 a. Volume 103, Issues 1-2, Pages 1-473 (29 Sep. 2004);
 b. Volume 102, Issue 1, Pages 1-177 (September 2004); and
 c. Volume 106, Issue 1, Pages 1-488 (29 Apr. 2005).

Tissue Characterization Using Chemical Sensors:

Chemical sensors detect the presence of various types of chemical compounds and states. For example, ions, such as, but not limited to, Na, K; dissolved gases, such as, but not limited to, Oxygen, carbon di-oxide; and Ph of solution.

Some of these sensors are further discussed in:

(i) Sensors: A comprehensive survey. Volume 2: Chemical and biochemical sensors, Part I. Ed. W. Gopel, J. Hesse, & J. N. Zenel (VCH, 1991);

(ii) Sensors: A comprehensive survey. Volume 3: Chemical and biochemical sensors, Part II. Ed. W. Gopel, J. Hesse, & J. N. Zenel (VCH, 1992); and (iii) Journal: Sensors & actuators B (chemical). Volume:
 a. Volume 103, Issues 1-2, Pages 1-473 (29 Sep. 2004);
 b. Volume 102, Issue 1, Pages 1-177 (September 2004);
 c. Volume 106, Issue 1, Pages 1-488 (29 Apr. 2005); and
 d. Volume 108, Issues 1-2, Pages 1-1000 (22 Jul. 2005).

Tissue Characterization Using Mechanical Sensors:

Mechanical sensors measure a physical property of the tissue in contact with the sensor. One example of a mechanical sensor uses, tactile sensing that measures the pressure sensed on the sensor surface. An optical tactile sensor having a transparent elastic tactile portion has been taught in U.S. Pat. No. 6,909,084 to Tachi and Kajimoto, whose disclosure is incorporated herein by reference, provides an optical tactile sensor with a tactile section and imaging means, the tactile section comprising a transparent elastic body and a plurality of groups of markers provided inside the elastic body, each marker group made up of a number of colored markers, with markers making up different marker groups having different colors for each group, and behavior of the colored markers when an object touches the elastic body being photographed by the imaging means. Preferably the marker groups have mutually different spatial arrangements.

Furthermore, mechanical sensors are discussed in: Sensors: A comprehensive survey. Volume 7: Mechanical sensors. Ed. W. Gopel, J. Hesse, & J. N. Zenel (VCH, 1994).

It will be appreciated that the method, in accordance with the present invention may adapted for human tissue and for animal tissue.

It will be appreciated that the method, in accordance with the present invention may performed during a surgical operation, wherein the external surface of the tissue is an incision surface.

Alternatively, the external surface of the tissue is skin.

Alternatively, the external surface of the tissue is lining of a lumen.

It is expected that during the life of this patent many relevant broad-band sensors, for tissue characterization will be developed and the scope of the term broad-band sensor, for tissue characterization is intended to include all such new technologies a priori.

As used herein the term "about" and "substantially" refer to ±20%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, any citation or identification of any reference in this application shall not be construed as an admission that such reference is available as prior art to the present invention.

What is claimed is:

1. A device for providing effective contact between a sensor and tissue, comprising:
   a structure;
   a duct system, associated with said structure, said duct system comprising two or more orifices at the proximal end of the structure; a suction source operatively connected to said duct system; said duct system and said suction source configured to exert a first force on a tissue at said orifices and to fix the tissue to said structure, so as to immobilize the tissue;
   a mechanism, associated with said structure, said mechanism comprising a piston, a spring, and a sensor; said sensor is on the proximal end of said piston; said mechanism configured to press the sensor against an external surface of the immobilized tissue and to thereby exert a second force on the immobilized tissue;
   at least one connection between the mechanism and the duct system; and
   said spring positioned between a portion of the piston and a portion of the structure, such that said spring is configured to regulate the second force when compressed, wherein said piston and structure are configured to cause the spring to be compressed via vacuum from the suction source when vacuum is applied to duct system;
   wherein said mechanism is configured to exert the second force in a direction opposite to said first force and to force the immobilized tissue against the sensor while the duct system and suction source immobilizes the tissue;
   wherein said structure, duct system, suction source, and mechanism combined are configured to bring about an effective contact between said sensor and the immobilized tissue by simultaneously immobilizing the tissue, pressing the sensor against the external surface of the immobilized tissue, and regulating the force applied by the sensor with compression of the spring controlled by the vacuum.

2. The device of claim 1, wherein said effective contact is a contact level of at least 95%.

3. The device of claim 1, wherein said effective contact is a contact level of at least 99%.

4. The device of claim 1, wherein said effective contact is a contact level of at least 99.8%.

5. The device of claim 1, wherein said sensor is configured to operate at a wavelength $\lambda$, and said sensor is configured for placement with an average distance t1, between the external surface of the tissue and said sensor being such that $t1<\lambda/3$.

6. The device of claim 1, wherein said sensor is configured to operate at a wavelength $\lambda$, and said sensor is configured for placement with an average distance t1, between the external surface of the tissue and said sensor being such that $t1<\lambda/10$.

7. The device of claim 1, wherein said sensor is configured to operate at a wavelength $\lambda$, and said sensor is configured for placement with an average distance t1, between the external surface of the tissue and said sensor being such that $t1<\lambda/100$.

8. The device of claim 1, wherein said sensor is configured for placement such that an average distance t1, between the external surface of the tissue and said sensor, is less than 500 Angstroms.

9. The device of claim 1, wherein said sensor is configured for placement such that an average distance t1, between the external surface of the tissue and said sensor, is less than 50 Angstroms.

10. The device of claim 1, wherein said sensor is configured for placement such that an average distance t1, between the external surface of the tissue and said sensor, is less than 5 Angstroms.

11. The device of claim 1, wherein said sensor is selected from the group consisting of an optical sensor, a Magnetic Resonance Imaging (MRI) sensor, a radiofrequency (RF) sensor, a microwave (MW) sensor, an X-ray sensor, an ultrasound sensor, a temperature sensor, an infrared thermography sensor, a biosensor, a chemical sensor, and a mechanical sensor.

12. The device of claim 1, wherein said spring is configured to regulate said second force while compressed by exerting a force on said piston in a respectively opposing direction to said second force.

13. A system for tissue characterization, comprising:
   a device for providing effective contact between a sensor and tissue, comprising:
   a structure;
   a duct system, associated with said structure, said duct system comprising two or more orifices at the proximal end of the structure; a suction source operatively connected to said duct system; said duct system and said suction source configured to exert a first force on a tissue at said orifices and to fix the tissue to said structure, so as to immobilize the tissue;
   a mechanism, associated with said structure, said mechanism comprising a piston, a spring, and a sensor; said sensor is on the proximal end of said piston;

said mechanism configured to press the sensor against an external surface of the immobilized tissue and to thereby exert a second force on the immobilized tissue;

at least one connection between the mechanism and the duct system; and said spring positioned between a portion of the piston and a portion of the structure, such that said spring is configured to regulate the second force when compressed, wherein said piston and structure are configured to cause the spring to be compressed via vacuum from the suction source when vacuum is applied to duct system;

wherein said mechanism is configured to exert the second force in a direction opposite to said first force and to force the immobilized tissue against the sensor while the duct system and suction source immobilizes the tissue;

wherein said structure, duct system, suction source, and mechanism combined are configured to bring about an effective contact between said sensor and the immobilized tissue by simultaneously immobilizing the tissue, pressing the sensor against the external surface of the immobilized tissue, and regulating the force applied by the sensor with compression of the spring controlled by the vacuum; and a signal analyzer, configured to be in signal communication with said sensor;

said signal analyzer configured to process an output signal from said sensor to provide said tissue characterization.

14. The system of claim 13, further comprising a signal generator configured to provide the sensor with an input signal.

15. The system of claim 13, and further comprising:
a computer, configured to be in signal communication with said signal analyzer; and
said computer configured to further process said output signal from said signal analyzer.

16. A method for providing effective contact between a sensor and tissue, comprising:
providing a device for providing effective contact between a sensor and tissue, comprising:
a structure;
a duct system, associated with said structure, said duct system comprising two or more orifices at the proximal end of the structure; a suction source operatively connected to said duct system; said duct system and said suction source configured to exert a first force on a tissue at said orifices and to fix the tissue to said structure, so as to immobilize the tissue;
a mechanism, associated with said structure, said mechanism comprising a piston, a spring, and a sensor; said sensor is on the proximal end of said piston;
said mechanism configured to press the sensor against an external surface of the immobilized tissue and to thereby exert a second force on the immobilized tissue;
at least one connection between the mechanism and the duct system; and
said spring positioned between a portion of the piston and a portion of the structure, such that said spring is configured to regulate the second force when compressed, wherein said piston and structure are configured to cause the spring to be compressed via vacuum from the suction source when vacuum is applied to duct system;

wherein said mechanism is configured to exert the second force in a direction opposite to said first force and to force the immobilized tissue against the sensor while the duct system and suction source immobilizes the tissue;

wherein said structure, duct system, suction source, and mechanism combined are configured to bring about an effective contact between said sensor and the immobilized tissue by simultaneously immobilizing the tissue, pressing the sensor against the external surface of the immobilized tissue, and regulating the force applied by the sensor with compression of the spring controlled by the vacuum;

fixing the tissue to said two or more orifices, thus immobilizing the tissue;

pressing said sensor against the external surface of the immobilized tissue, thereby exerting said second force on the immobilized tissue;

compressing the spring via vacuum, and regulating the compression of the spring via the applied vacuum; and simultaneously fixing the tissue, pressing the sensor and compressing and regulating the spring, and thus bringing about said effective contact between said sensor and the immobilized tissue.

17. A method for providing effective contact between a sensor and tissue, comprising:
applying vacuum to a duct system comprising two or more orifices at the proximal end of a structure, the duct system operatively connected to a suction source, said suction source providing vacuum to said duct system;
fixing the tissue to all of the two or more orifices at the proximal end of a structure, thus exerting a first force on the tissue at all of said orifices and immobilizing the tissue;
pressing a sensor against the external surface of the immobilized tissue, wherein said sensor is on the proximal end of a piston, thereby exerting a second force on the immobilized tissue;
applying vacuum through at least one connection from the duct system to a spring tunnel that contains a spring, said spring surrounding a portion of the piston and contacting a proximal facing surface of the distal portion of the piston;
compressing the spring in the spring tunnel with the application of the vacuum, wherein said compressing of said spring limits the second force;
regulating the compression of the spring via the vacuum applied through the at least one connection from the duct system to the spring tunnel; and
simultaneously fixing the tissue, pressing the sensor and compressing and regulating the spring, and thus bringing about said effective contact between said sensor and the immobilized tissue.

18. A device for providing effective contact between a sensor and tissue, comprising:
a structure;
a first mechanism, associated with said structure, said first mechanism comprising a suction source and a duct system with two or more orifices at the proximal end of the structure, said first mechanism configured to exert a first force on a tissue and to fix the tissue to said structure, so as to immobilize the tissue;
a second mechanism, associated with said structure, said second mechanism comprising a piston, a spring, a spring tunnel, and a sensor; said sensor is on the proximal end of said piston; said second mechanism configured to press the sensor against an external surface of the immobilized tissue and to thereby exert a second force on the immobilized tissue;

at least one connection between the spring tunnel of the second mechanism and the duct system of the first mechanism; and said spring positioned in the spring tunnel between a portion of the piston and a portion of the structure, such that said spring is configured to regulate the second force when compressed, wherein said spring tunnel and piston are configured to cause the spring to be compressed via vacuum from the suction source when vacuum is applied to said duct system;

wherein said second mechanism is configured to exert the second force in a direction opposite to said first force and to force the immobilized tissue against the sensor while the first mechanism immobilizes the tissue;

wherein said structure, first mechanism, and second mechanism combined are configured to cause an effective contact between said sensor and the immobilized tissue by simultaneously immobilizing the tissue, pressing the sensor against the external surface of the immobilized tissue, and regulating the force applied by the sensor with compression of the spring controlled by the vacuum.

19. A device for providing effective contact between a sensor and tissue, comprising:

a structure;

a duct system, associated with said structure, said duct system comprising two or more orifices at the proximal end of the structure; a suction source operatively connected to said duct system; said duct system and said suction source configured to exert a first force on a tissue at said orifices and to fix the tissue to said structure, so as to immobilize the tissue;

a mechanism, associated with said structure, said mechanism comprising a piston, a spring, and a sensor; said sensor is on the proximal end of said piston; said mechanism configured to press the sensor against an external surface of the immobilized tissue and to thereby exert a second force on the immobilized tissue;

at least one connection between the mechanism and the duct system; and said spring positioned between a portion of the piston and a portion of the structure, such that said spring is configured to regulate the second force when compressed, wherein said piston and structure are configured to cause the spring to be compressed via vacuum from the suction source when vacuum is applied to duct system;

wherein said mechanism is configured to exert the second force in a direction opposite to said first force and to force the immobilized tissue against the sensor while the duct system and suction source immobilizes the tissue;

wherein said structure, duct system, suction source, and mechanism combined are configured to bring about an effective contact between said sensor and the immobilized tissue by simultaneously immobilizing the tissue, pressing the sensor against the external surface of the immobilized tissue, and regulating the force applied by the sensor with compression of the spring controlled by the vacuum;

wherein said sensor is configured to operate at a wavelength $\lambda$, and said sensor is configured for placement with an average distance t1, between the external surface of the tissue and said sensor, such that $t1 < \lambda/3$.

20. A device for providing effective contact between a sensor and tissue, comprising:

a structure;

a first mechanism, associated with said structure, said first mechanism comprising a suction source and a duct system with two or more orifices at the proximal end of the structure, said first mechanism configured to exert a first force on a tissue and to fix the tissue to said structure, so as to immobilize the tissue;

a second mechanism, associated with said structure, said second mechanism comprising a piston, a spring, a spring tunnel, and a sensor; said sensor is on the proximal end of said piston; said second mechanism configured to press the sensor against an external surface of the immobilized tissue and to thereby exert a second force on the immobilized tissue;

at least one connection between the spring tunnel of the second mechanism and the duct system of the first mechanism; and said spring positioned in the spring tunnel between a portion of the piston and a portion of the structure, such that said spring is configured to regulate the second force when compressed, wherein said spring tunnel and piston are configured to cause the spring to be compressed via vacuum from the suction source when vacuum is applied to said duct system;

wherein said second mechanism is configured to exert the second force in a direction opposite to said first force and to force the immobilized tissue against the sensor while the first mechanism immobilizes the tissue;

wherein said structure, first mechanism, and second mechanism combined are configured to cause an effective contact between said sensor and the immobilized tissue by simultaneously immobilizing the tissue, pressing the sensor against the external surface of the immobilized tissue, and regulating the force applied by the sensor with compression of the spring controlled by the vacuum;

wherein said sensor is configured to operate at a wavelength $\lambda$, and said sensor is configured for placement with an average distance t1, between the external surface of the tissue and said sensor, such that $t1 < \lambda/3$.

21. A device for providing effective contact between a sensor and tissue, comprising:

a structure;

a duct system, associated with said structure, said duct system comprising two or more orifices at the proximal end of the structure; a suction source operatively connected to said duct system; said duct system and said suction source configured to exert a first force on a tissue at said orifices and to fix the tissue to said structure, so as to immobilize the tissue;

a mechanism, associated with said structure, said mechanism comprising a piston, a spring, and a sensor; said sensor is on the proximal end of said piston; said mechanism configured to press the sensor against an external surface of the immobilized tissue and to thereby exert a second force on the immobilized tissue;

at least one connection between the mechanism and the duct system; and said spring positioned between a portion of the piston and a portion of the structure, such that said spring is configured to regulate the second force when compressed, wherein said piston and structure are configured to cause the spring to be compressed via vacuum from the suction source when vacuum is applied to duct system;

wherein said mechanism is configured to exert the second force in a direction opposite to said first force and to force the immobilized tissue against the sensor while the duct system and suction source immobilizes the tissue;

wherein said structure, duct system, suction source, and mechanism combined are configured to bring about an effective contact between said sensor and the immobilized tissue by simultaneously immobilizing the tissue, pressing the sensor against the external surface of the immobilized tissue, and regulating the force applied by the sensor with compression of the spring controlled by the vacuum;

wherein said effective contact is a contact level of at least 95%.

22. The device of claim 21, wherein said sensor is one member of the group of sensors consisting of: an optical sensor, an MRI sensor, an RF sensor, a MW sensor, an X-ray sensor, an ultrasound sensor, an infrared thermography sensor, a biosensor, a chemical sensor, and a mechanical sensor.

23. A device for providing effective contact between a sensor and tissue, comprising:
a structure;
a first mechanism, associated with said structure, said first mechanism comprising a suction source and a duct system with two or more orifices at the proximal end of the structure, said first mechanism configured to exert a first force on a tissue and to fix the tissue to said structure, so as to immobilize the tissue;
a second mechanism, associated with said structure, said second mechanism comprising a piston, a spring, a spring tunnel, and a sensor; said sensor is on the proximal end of said piston; said second mechanism configured to press the sensor against an external surface of the immobilized tissue and to thereby exert a second force on the immobilized tissue;
at least one connection between the spring tunnel of the second mechanism and the duct system of the first mechanism; and
said spring positioned in the spring tunnel between a portion of the piston and a portion of the structure, such that said spring is configured to regulate the second force when compressed, wherein said spring tunnel and piston are configured to cause the spring to be compressed via vacuum from the suction source when vacuum is applied to said duct system;

wherein said second mechanism is configured to exert the second force in a direction opposite to said first force and to force the immobilized tissue against the sensor while the first mechanism immobilizes the tissue;

wherein said structure, first mechanism, and second mechanism combined are configured to cause an effective contact between said sensor and the immobilized tissue by simultaneously immobilizing the tissue, pressing the sensor against the external surface of the immobilized tissue, and regulating the force applied by the sensor with compression of the spring controlled by the vacuum;

wherein said effective contact is a contact level of at least 95%.

* * * * *